United States Patent
Anderson

(10) Patent No.: US 9,588,126 B2
(45) Date of Patent: Mar. 7, 2017

(54) MULTIPURPOSE MASS SPECTROMETRIC ASSAY PANELS FOR PEPTIDES

(71) Applicant: SISCAPA Assay Technologies, Inc., Washington, DC (US)

(72) Inventor: N. Leigh Anderson, Washington, DC (US)

(73) Assignee: SISCAPA Assay Technologies, Inc., Washington, DC (US)

( * ) Notice: Subject to any disclaimer, the term of this patent is extended or adjusted under 35 U.S.C. 154(b) by 0 days.

(21) Appl. No.: 14/584,606

(22) Filed: Dec. 29, 2014

(65) Prior Publication Data

US 2015/0108344 A1   Apr. 23, 2015

Related U.S. Application Data

(63) Continuation of application No. PCT/US2013/048384, filed on Jun. 27, 2013.

(60) Provisional application No. 61/665,217, filed on Jun. 27, 2012.

(51) Int. Cl.

| | |
|---|---|
| *G01N 33/68* | (2006.01) |
| *G01N 27/62* | (2006.01) |
| *H01J 49/00* | (2006.01) |
| *G01N 33/50* | (2006.01) |
| *G01N 33/80* | (2006.01) |
| *G01N 33/96* | (2006.01) |

(52) U.S. Cl.
CPC ......... *G01N 33/6848* (2013.01); *G01N 27/62* (2013.01); *G01N 33/5094* (2013.01); *G01N 33/80* (2013.01); *G01N 33/96* (2013.01); *H01J 49/0036* (2013.01)

(58) Field of Classification Search
None
See application file for complete search history.

(56) References Cited

U.S. PATENT DOCUMENTS

| | | |
|---|---|---|
| 6,106,732 A | 8/2000 | Johnston et al. |
| 6,187,531 B1 | 2/2001 | Tyrrell |
| 6,258,045 B1 | 7/2001 | Ray et al. |
| 7,632,686 B2 | 12/2009 | Anderson |
| 2006/0154318 A1 | 7/2006 | Anderson |
| 2010/0075338 A1 | 3/2010 | Vessey et al. |
| 2011/0159530 A1 | 6/2011 | Pass et al. |

FOREIGN PATENT DOCUMENTS

| | | |
|---|---|---|
| WO | 2011063389 A2 | 5/2011 |
| WO | 2011063389 A3 | 5/2011 |
| WO | 2011116028 | 9/2011 |

OTHER PUBLICATIONS

European Search Report in European Application No. 13810471.6, mailing date Mar. 17, 2016, 7 pages.
Wennecke, G.: "Hematocrit—A review of different analytical methods", Hematocrit, Sep. 2004, 11 pages.
Agilent Technologies Application Note 5990-7360EN Published Jan. 25, 2011; https://www.chem.agilent.com.
Anderson et al., "Quantitative Mass Spectrometric Multiple Reaction Monitoring Assays for Major Plasma Proteins*," Molecular & Cellular Proteomics, vol. 5.4, pp. 573-588. Dec. 6, 2005.
Bikoue et al., Clin. Immunol. and Iimmunopath. 84, 56-67 (1997).
International Search Report and Written Opinion for International Application PCT/US2013/048384; Applicant, Siscapa Assay Technologies, Inc. Mail Date Nov. 29, 2013; pp. 11.
Youhnovski et al., Rapid Commun. Mass Spectrum 25:2951-2958.
Youhnovski et al., Rapid Commun. Mass Spectrum 25:2951-2958, year 2011.

*Primary Examiner* — Jacob Cheu
(74) *Attorney, Agent, or Firm* — Edell, Shapiro & Finnan, LLC

(57) ABSTRACT

Methods are provided for estimating the relative amounts of identifiable compartments, such as different types of cells or cell components, within a biological sample. The methods use mass spectrometric analysis in quantitate compartment-specific molecules and thereby allow calculation of the amount of each compartment that is present in a biological sample. The methods can, for example, provide a measurement of hematocrit from a dried blood sample.

12 Claims, 2 Drawing Sheets

US 9,588,126 B2

MULTIPURPOSE MASS SPECTROMETRIC ASSAY PANELS FOR PEPTIDES

CROSS REFERENCE TO RELATED APPLICATIONS

This application is a continuation of International Application No. PCT/US13/48384, filed Jun. 27, 2013, which claims the benefit of U.S. provisional application 61/665,217,602, entitled Multipurpose Mass Spectrometric Assay Panels for Peptides filed on Jun. 27, 2012 each of which are herein incorporated by referenced in their entireties.

BACKGROUND

Mass spectrometry has been used for the measurement of established and candidate biomarker proteins but has not been widely used for analyzing proteins in whole blood and dried blood spots.

SUMMARY

Quantitative assays are provided for measuring proteins in complex biological samples, including in clinical specimens such as human blood (in both liquid and dried forms) and other proteinaceous samples including, for example, tissues, secretions, and body fluids of all living things, as well as samples prepared from heterogeneous mixtures of these. In particular, methods are provided for using protein measurements to obtain information on the relative amounts of larger molecular aggregates including cells, particles and soluble compartments in biological samples.

Many methods exist for the measurement of compartments and particles in biological samples. In blood, for example, a smear can be prepared on a glass slide and dried, stained with hematoxylin and eosin, and examined by optical microscopy to determine, by counting, the relative number of red cells, lymphocytes, monocytes, eosinophils and neutrophils present in the sample. Blood hematocrit (the approximate proportion of the volume of blood occupied by red cells) can be measured by centrifuging a capillary tube filled with blood (pelleting the heavy red cells) and measuring the length in the capillary of the red cell pellet compared to the length of the original blood sample (essentially a relative volume ratio). Automated devices are also used clinically to count various cells and particles in blood (e.g., "Coulter counters", flow cytometers, and the like). By staining blood leukocytes with fluorescently labeled antibodies specific for certain types of leukocytes, flow cytometers can count the numbers of a variety of such types in research and clinical blood samples, an example being the counting of CD4 positive lymphocytes in the management of HIV/AIDS.

However, in circumstances where the cells are broken or dissolved much of the information as to the relative amounts or numbers of these compartments, cells or particles is lost. For example when blood is dried and redissolved, when blood is dissolved to solubilize its protein constituents for analysis, or when a solid tissue is homogenized, the contents of the component compartments are at least partially mixed, preventing measurement of the relative amounts or numbers of the compartments by conventional means.

Methods are provided that measure the relative amounts of compartments, cells and particles in a complex protein sample in which mixing of compartments has occurred, during, for example, sample preparation. By measuring "compartment specific molecules" (CSM) for one or more compartments, it is possible to reconstruct ratios between the amounts of compartments in the sample, anchor, using prior information about the amount of a CSM in a compartment, the absolute amount of a compartment in a sample. These methods allow measurement of the compartment composition of complex samples such as blood, solid tissues, and combinations of liquid and solid tissues. The results provide important clinical information such as a complete blood count from a sample like a dried blood spot, in which no intact cells remain, and allow normalization of the results of other assays that depend on knowing the relative size of various compartments such as plasma in whole blood.

What is provided is a method for measuring the relative amounts of a first and a second compartment of a biological sample, comprising:

i) measuring in the sample the amount of a first compartment-specific molecule (CSM) specific to the first compartment, ii) measuring in the sample the amount of a second CSM specific to the second compartment, iii) calculating the volume of the first compartment in the sample using the amount of the first CSM and a pre-established value of the expected concentration of the first CSM in the first compartment, iv) calculating the volume of the second compartment in the sample using the amount of the second CSM and a pre-established value of the expected concentration of the second CSM in the second compartment, and v) comparing the volumes of the first and second compartments, thereby deriving the relative amounts of the compartments in the sample.

The sample may be a blood sample, and the first compartment may be plasma and the second compartment red blood cells. The CSM specific to the plasma compartment may be selected from the group consisting of HSA, immunoglobulins, transferrin, and alpha-2-macroglobulin. The CSM may be measured in a proteolytic digest of the sample by quantitative mass spectrometry of one or more monitor peptides selected from the group consisting of Seq ID 1-5 (HSA); Seq ID 6-10 (immunoglobulins); Seq ID 11-15 (transferrin); and Seq ID 16-20 (alpha-2-macroglobulin. The CSM specific to the red blood cell compartment may be is selected from the group consisting of hemoglobin alpha chain, hemoglobin beta chain, and carbonic anhydrase 1. The CSM is may be measured in a proteolytic digest of the sample by quantitative mass spectrometry of one or more monitor peptides selected from the group consisting of Seq ID 21-24 (Hb alpha), Seq ID 25-29 (Hb beta) and Seq ID 30-34 (carbonic anhydrase 1).

The quantitative mass spectrometry measurement can be obtained as a ratio of (i) signal observed for one or more monitor peptides to (ii) the signal observed for the respective stable isotope labeled same-sequence internal standard SIS peptide added to the digest in known amount. The relative proportions may be used to calculate the hematocrit value of the blood sample.

The compartments m the sample may have been mixed prior to analysis by, for example, cell lysis. The compartment volumes can be used to obtain compartment concentrations of analyte CSM's different from the first and second CSM's.

The sample may be a dried blood sample. The analyte CSM's may be proteins in the plasma compartment, and plasma concentrations of the CSM's can be calculated by dividing the measured amount of the analyte CSM by the plasma compartment volume.

The sample may be a sample of tissue derived from a vertebrate animal, where the first compartment is plasma or red blood cells, and where the second compartment is selected from cell types of the organism excluding, those occurring in blood.

The relative proportion of the compartments may be used to estimate the proportion of blood within the tissue. The volumes of the first and second compartments may be combined, thereby deriving the volume of the sample.

The sample may be a sample of blood dried on or within a substrate and the sample volume may be the volume of blood dried on or within the substrate. The volume of blood dried may be used to obtain sample concentrations of analyte CSM's different from the first and second CSM's.

Also provided is a method for measuring the number of cells constituting a compartment of a multi-compartment biological sample comprising:

i) measuring in the sample the amount of, or the number of molecules of, a first CSM specific to the cells, and ii) calculating the number of the cells in the sample by dividing the measured number of molecules by the pre-established average number of CSM molecules occurring in each of the cells of the compartment.

The sample may be blood and the compartment is selected from the group consisting of leukocytes, B lymphocytes, T lymphocytes, helper T lymphocytes, NK cells, monocytes, neutrophils, eosinophils, and platelets.

The CSM for leukocytes may be CD45 or L-plastin. The CSM may be measured in a proteolytic digest of the sample by quantitative mass spectrometry of one or More monitor peptides selected from among Seq ID 35-39 (CD45) and Seq ID 40-44 (L-plastin).

The CSM for B lymphocytes may be CD19, CD20, CD22 and CD38. The CSM may be measured in a proteolytic digest of the sample by quantitative mass spectrometry of one or more monitor peptides selected from the group consisting of Seq ID 45-49 (CD19); Seq 50-52 (CD20); Seq ID 58-62 (CD22) and Seq ID 53-57 (CD38).

The CSM for T lymphocytes may be CD3. The CSM may be measured in a proteolytic digest of the sample by quantitative mass spectrometry of one or more monitor peptides selected from Seq ID 63-67 (CD3).

The CSM for helper T lymphocytes may be CD4. The CSM may be measured in a proteolytic digest of the sample by quantitative mass spectrometry of one or more monitor peptides selected from Seq ID 73-77 (CD4)

The CSM for NK cells may be CD56. CSM may be measured in a proteolytic digest of the sample by quantitative mass spectrometry of one or more monitor peptides selected from Seq ID 68-72 (CD56).

The CSM for monocytes may be selected from CD11a, CD14 and CD64. The CSM may be measured in a proteolytic digest of the sample by quantitative mass spectrometry of one or more monitor peptides selected from the group consisting of Seq ID 86-90 (CD11a); Seq ID 81-85 (CD14) and Seq ID 78-80 (CD64).

The CSM for neutrophils may be selected from the group consisting of MPO, neutrophil elastase, defensin alpha 1 and MMP8. The CSM may be measured in a proteolytic digest of the sample by quantitative mass spectrometry of one or more monitor peptides selected from the group consisting of Seq ID 91-95 (MPO); Seq ID 96-99 (neutrophil elastase); Seq ID 100-102 (defensin alpha 1) and Seq ID 103-107 (MMP8).

The CSM for eosinophils may be PRG2. The CSM may be measured in a proteolytic digest of the sample by quantitative mass spectrometry of one or more monitor peptides selected from Seq ID 108-112 (PRG2).

The CSM for platelets may be selected from PF-4, CD41, CD61, CD62 and platelet basic protein. The CSM may be measured in a proteolytic digest of the sample by quantitative mass spectrometry of one or more monitor peptides selected from the group consisting of Seq ID 111-117 (PF-4); Seq ID 128-132 (CD41); Seq ID 118-122 (CD61); Seq ID 133-137 (CD62); and Seq ID 123-127 (platelet basic protein).

The CSM may be measured in a proteolytic digest of the sample by quantitative mass spectrometry of one or more monitor peptides selected from the group consisting of Seq ID 35-39 (CD45); Seq ID 40-44 (L-plastin); Seq ID 45-49 (CD19); Seq ID 50-52 (CD20); Seq ID 58-62 (CD22), Seq ID 53-57 (CD38), Seq ID 63-67 (CD3), Seq ID 73-77 (CD4), Seq ID 68-72 (CD56), Seq ID 86-90 (CD11a); Seq ID 81-85 (CD14), Seq ID 78-80 (CD64), Seq ID 91-95 (MPO); Seq ID 96-99 (neutrophil elastase); Seq ID 100-102 (defensin alpha 1), Seq 103-107 (MMP8), Seq ID 108-112 (PRG2), Seq ID 113-117 (PF-4); Seq ID 128-132 (CD41); Seq ID 118-122 (CD61); Seq ID 133-137 (CD62); and Seq ID 123-127 (platelet basic protein).

Also provided is a method for measuring the number of cells constituting each of a multiplicity of compartments in a blood sample comprising:

i) measuring in the sample the amount of, or equivalently the number of molecules of, a compartment-specific molecule (CSM) specific to cells of each of the compartments, and ii) calculating the number of the cells in each of the compartments of the sample by dividing the measured number of molecules by the respective pre-established average number of CSM molecules occurring in each of the cells of the compartment, where the compartments are selected from the group consisting of red blood cells, B lymphocytes, T lymphocytes, helper T lymphocytes, NK cells, monocytes, neutrophils, eosinophils, and platelets.

Further provided is a method for measuring the relative amounts of a first and a second compartment of a biological sample comprising:

i) selecting a first monitor peptide that is proteotypic for a first protein whose amount in the sample is contributed predominantly by the first compartment.

ii) selecting a second monitor peptide that is proteotypic for a second protein whose amount in the sample is contributed predominantly by the second compartment, iii) digesting the sample by means of a proteolytic process to produce a digest, iv) adding to the digest labeled versions of the first and second peptides, differing respectively from the first and second peptides by a mass increment, in known amounts, v) measuring the amounts of the first monitor peptide and the labeled version of the first monitor peptide using a mass spectrometer, dividing the measured amount of the first monitor peptide by the measured amount of the labeled version of the first monitor peptide, and multiplying the ratio by the known amount of the labeled version of the first peptide to yield an amount of the first peptide in the digest, vi) measuring the amounts of the second monitor peptide and the labeled version of the second monitor peptide using a mass spectrometer, dividing the measured amount of the second monitor peptide by the measured amount of the labeled version of the second monitor peptide, and multiplying the ratio by the known amount of the labeled version of the second peptide to yield an amount of the second peptide in the digest, vii) calculating the relative amounts of the first and second compartments in the sample using the relative amounts of the first and second peptides in the digest, together with previous measurements of the concentrations of the first peptide, or the first protein, in the first compartment and of the second peptide, or the second protein, in the second compartment.

Also provided is a method for measuring the amount of a specific compartment contained in a biological sample comprising i) selecting a marker protein whose amount in the sample is contributed predominantly by the compartment, and whose concentration in the compartment is known, ii) selecting a monitor peptide that is proteotypic for the marker protein, iii) digesting the sample process to produce a proteolytic digest, iv) adding to the digest a known amount of a labeled version of the monitor peptide, differing from the monitor peptides by a mass increment, v) measuring the amount of the monitor peptide and the labeled version of the monitor peptide using a mass spectrometer, dividing the measured amount of the monitor peptide by the measured amount of the labeled version of the monitor peptide and multiplying by the known amount of die labeled version of the peptide to calculate an amount of the monitor peptide in the digest, vi) calculating the relative amount of the compartment in the sample using the amount of the peptide in the digest and previous measurement(s) of the concentrations of the peptide, or the protein, in the compartment.

The sample may be whole blood and the compartment is one or more of the cells or particulate components of blood, where the compartment is selected from the group consisting of erythrocytes, platelets, lymphocytes (including the many specific subtypes of lymphocytes), neutrophils, eosinophils, monocytes, and macrophages.

The compartment may be a blood cell subset and the marker protein may be a known cell surface marker of the blood cell subset.

The cell surface marker may a CD antigen or a granule protein.

The amounts of a plurality of marker proteins and/or protcotypic peptides can be combined in an algorithm to provide a more representative estimate of the amount of the compartment in the sample.

The amounts of a plurality of highly abundant plasma proteins can be used to estimate the proportion of plasma in a sample of whole blood, and where the plasma proteins are selected from the group consisting of albumin, transferrin, haptoglobin, IgG, IgA, alpha1-antitrypsin, fibrinogen, alpha2-macroglobulin, alpha1-acid glycoprotein, complement C3, IgM, apolipoprotein AI, apolipoprotein AII, and transthyretin.

The sample may be whole blood and the compartment may be plasma or CD4+ lymphocytes.

The sample may be a solid tumor and the compartment may be lymphocytes infiltrating the tumor.

Also provided is a method for correcting the measured concentration of a protein or peptide in a sample comprising a plurality of compartments, where the protein or peptide is contributed primarily by one compartment of the sample, comprising measuring the concentration or amount of the protein or peptide in a digest of the sample, and calculating the concentration or amount of the protein or peptide in the compartment by dividing the concentration or amount by the relative amount of the compartment in the sample.

Also provided is a method for correcting the measured concentration of a protein or peptide in a sample comprising a plurality of compartments, where the protein or peptide is contributed primarily by one compartment of the sample, comprising measuring the concentration or amount of the protein or peptide in a digest of the sample, and calculating the concentration or amount of the protein or peptide in the compartment by dividing the concentration or amount by the relative amount of the compartment in the sample, where the relative amount of the compartment is calculated using the method of claim 40.

DETAILED DESCRIPTION

Figure 1:
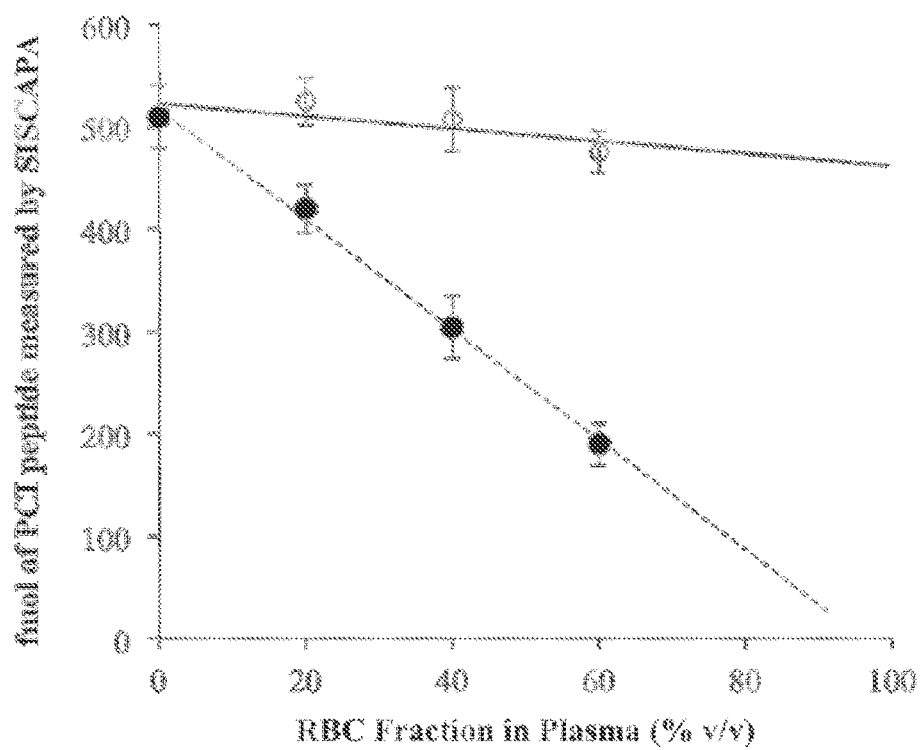
FIG. 1. Shows a plot of the amount of protein C inhibitor detected in 4 aliquots of a blood sample adjusted to different hematocrit levels (0, 20, 40 and 60%), either before (filled symbols) or after (open symbols) normalization for hematocrit.

The term "amount", "concentration" or "level" of an analyte or internal standard means the physical quantity of the substance referred to, either in terms of mass (or equivalently moles) or in terms of concentration (the amount of mass or moles per volume of a solution or liquid sample).

The term "analyte" or "ligand" refers to a molecule, or component, piece, fragment or section of a molecule that is to be measured or quantitated in a sample. An analyte may thus be, for example, a protein, a peptide derived from a protein by digestion or other fragmentation technique, a small molecule (such as a hormone, a metabolite, a drug, a drug metabolite) or a nucleic acid (DNA, RNA, or fragment thereof produced by an enzymatic, chemical or other fragmentation process).

The term "antibody" means a monoclonal or monospecific polyclonal immunoglobulin protein such as IgG or IgM. An antibody may be a whole antibody or antigen-binding antibody fragment derived from a species (e.g., rabbit or mouse) commonly employed to produce antibodies against a selected antigen, or may be derived from recombinant methods such as protein expression, and phagelvirus display. See, e.g., U.S. Pat. Nos. 7,732,168; 7,575,896; and 7,431,927, which describe preparation of rabbit monoclonal antibodies. Antibody fragments may be any antigen-binding fragment that can be prepared by conventional protein chemistry methods or may be engineered fragments such as scFv, diabodies, mini bodies and the like. It will be understood that other classes of molecules such as DNA and RNA aptamers configured as specific and high affinity binding agents may, be used as alternatives to antibodies or antibody fragments in appropriate circumstances.

The term "bind" or "react" means any physical attachment or close association, which may be permanent or temporary. Generally, reversible binding includes aspects of charge interactions, hydrogen bonding, hydrophobic forces, van der Waals forces etc., that facilitate physical attachment between the molecule of interest and the analyte being measuring. The "binding" interaction may be brief as in the situation where binding causes a chemical reaction to occur. Reactions resulting from contact between the binding agent and the analyte are also within the definition of binding for the purposes of the present technology, provided they can be later reversed to release a monitor fragment.

The term "binding agent" means a molecule or substance having an affinity for one or more analytes, and includes antibodies (for example polyclonal, monoclonal, single chain, and modifications thereof), aptamers (made of DNA, RNA, modified nucleotides, peptides, and other compounds), and the like. "Specific binding agents" are those with particular affinity for a specific analyte molecule.

The terms "clinical reference range" and "clinical reference interval" mean the range of abundance or concentration values of an analyte that are deemed to be within the "normal" clinical range. Such ranges frequently are established by determination of analyte levels in a normal population, and the clinical reference range typically determined as the central 95% of the resulting histogram (with 2.5% of the population above and 2.5% below the resulting high and low values). As used here, these terms also refer to ranges whose bounds are defined by clinical features other than the distribution of results in normal individuals (e.g., the population reference range in diabetic patients), and clinical ranges based on a patient's prior test values for the same or other analytes, alone or in combination with population test data. A variety of statistical approaches can be used to calculate such ranges from analyte measurements, and this advantageously can be done prior to their application in the design of an assay or the determination of an amount of internal standard to use in the assay. As in the case of a single test evaluation threshold, it will be understood that a clinical reference interval for use in a specific test can be set based on results obtained using the specific test or an equivalent methodology, in order that any analytical biases inherent in the test are reflected in the threshold.

The term "carrier" means a carrier molecule, a carrier particle or a carrier surface.

The term "compartment" means a portion of a complex sample delimited in the natural state from other parts of the sample by physical separation (e.g., by a membrane or membranes) or by a bulk physical property allowing easy separability. A compartment can be, for example, a cell or a subcellular component. Thus, using blood as an example, identifiable compartments include the plasma, red blood cells, neutrophils, lymphocytes, nuclei of lymphocytes, mitochondria of lymphocytes, high-density lipoprotein particles, cell-derived microparticles, and the like. Various classes of lymphocytes can be isolated using antibodies to class-specific surface antigens, while lipoproteins can be isolated from plasma by centrifugation (because of their low buoyant density compared to plasma). In other tissues, compartments include the various cell types of which the tissue is composed (e.g., hepatocytes and Kupffer cells in liver), and other fluids (e.g., synovial or cerebrospinal fluids). Molecules derived from these compartments can become mixed if the physical barriers between them are ruptured, made permeable or removed, such as occurs in the drying of a dried blood spot, or if the sample is solubilized, such as occurs on the addition of detergent or water to blood or when a tissue sample is homogenized or heated to near boiling.

The term "compartment-specific molecule" or "compartment-specific marker" or "CSM" means a molecular species, such as a protein, metabolite, RNA molecule or the like that is predominantly present in one of the compartments that make up a complex sample such as blood or tissue. A useful CSM is one in which the preponderance of the CSM in the sample is associated with or contained within the sample compartment whose amount is to be estimated. A preferred CSM is greater than 80% associated with the compartment to be measured, meaning that more than 80% of the CSM molecules in the sample are physically associated with or contained within the compartment to be measured. A more preferred CSM is greater than 90% associated with the compartment to be measured; and a most preferred CSM is greater than 95% associated with the compartment to be measured. In the context of a CSM, the term "specific" is thus defined in relation to other compartments occurring in the same sample. Hence a protein that is predominantly located within monocytes in blood (e.g., 85% of the protein in normal blood is within monocytes) but also occurs in significant amounts in liver tissue is a CSM in the context of blood, but may not be a CSM in the context of a liver biopsy containing both liver cells and blood. A useful CSM may occur in association with other compartments in other sample types, provided it shows this strong association with the relevant compartment in the sample of interest.

A "complete blood count" means a common clinical procedure used to determine the numbers of various functionally distinct types of cells and particles in blood. These include red cells, lymphocytes, monocytes, neutrophils, eosinophils, basophils and platelets.

A "secreted compartment-specific molecule" or "secreted compartment-specific marker" is a CSM that can, under some natural circumstances, be released front its compartment into another compartment, for example plasma.

The term "denaturant" includes a range of chaotropic and other chemical agents that act to disrupt or loosen the 3-D structure of proteins without breaking covalent bonds, thereby rendering them more susceptible to proteolytic treatment. Examples include urea, guanidine hydrochloride, ammonium thiocyanate, trifluoroethanol and deoxycholate, as well as solvents such as acetonitrile, methanol and the like. The concept of denaturant includes non-material influences capable of causing perturbation to protein structures, such as heat, microwave irradiation, ultrasound, and pressure fluctuations.

The term "electrospray ionization" (ESI) refers to a method for the transfer of analyte molecules in solution into the gas and ultimately vacuum phase through use of a combination of liquid deli very to a pointed exit and high local electric field.

The term "immobilized enzyme" means any form of enzyme that is fixed to the matrix of a support by covalent or non-covalent interaction such that the majority of the enzyme remains attached to the support of the membrane.

The terms "particle" or "bead" mean any kind of particle in the size range between 10 nm and lens, and includes magnetic particles and beads.

The term "MALDI" means Matrix Assisted Laser Desorption Ionization and related techniques such as SELDI, and includes any technique that generates charged analyte ions from a solid analyte-containing material on a solid support under the influence of a laser or other means of imparting a short energy pulse.

The term "Mass spectrometer" for "MS") means an instrument capable of separating, molecules on the basis of their mass m, or m/z where z is molecular charge, and then detecting them. In one embodiment, mass spectrometers detect molecules quantitatively. An MS may use one, two, or more stages of mass selection. In the case of multistage selection, some means of fragmenting the molecules is typically used between stages, so that later stages resolve fragments of molecules selected in earlier stages. Use of multiple stages typically affords improved overall specificity compared to a single stage device. Often, quantitation of molecules is performed in a triple-quadrupole mass spectrometer using the method referred to as 'Multiple Reaction Monitoring' or "MRM mass spectrometry" in which measured molecules are selected first by their intact mass and secondly, after fragmentation, by the mass of a specific expected molecular fragment. However it will be understood herein that a variety of different MS configurations may be used to analyze the molecules described. Possible configurations include, but are not limited to, MALDI instruments including MALDI-TOF, MALDI-TOF/TOF, and MALDI-TQMS, and electrospray instruments including EST:TQMS and ESI-QTOF, in which TOF means time of flight, TQMS means triple quadrupole MS, and QTOF means quadrupole TOF.

The term "monitor fragment" refers to any portion of an analyte, but not including the whole analyte, that can be produced by a reproducible fragmentation process and whose abundance or concentration can be used as a surrogate for the abundance or concentration of the analyte.

The term "monitor peptide" or "target peptide" means a peptide chosen as a monitor fragment of a protein or peptide.

The term "Natural" or "Nat" moans the form of a peptide that is derived from a natural biological sample by proteolytic digestion and which contains approximately natural abundances of elemental isotopes. Nat peptides typically do not contain appreciable amounts of a stable isotope label such as a label intentionally incorporated in SIS internal standards.

The term "proteolytic treatment" or "enzyme" may refer any of a large number of different enzymes, including trypsin, chymotrypsin, lys-C, v8 and the like, as well as chemicals, such as cyanogen bromide, that, in the context of the methods described herein, acts to cleave peptide bonds in a protein or peptide in a sequence-specific manner, generating a collection of shorter peptides (a digest).

The term "proteotypic peptide" means a peptide whose sequence is unique to a specific protein in an organism, and therefore may be used as a stoichiometric surrogate for the protein, or at least for one or more forms of the protein in the case of a protein with splice variants.

The term "sample" means any complex biologically-generated sample derived from humans, other animals, plants or microorganisms, or any combinations of these sources. "Complex digest" means a proteolytic digest of any of these samples resulting from use of a proteolytic treatment.

The terms "SIS", "stable isotope standard" and "stable isotope labeled version of a peptide or protein analyte" mean a peptide or protein, such as a peptide or protein basing a unique sequence that is identical or substantially identical to that of a selected peptide or protein analyte, and including a label of some kind (e.g., a stable isotope) that allows its use as an internal standard for mass spectrometric quantitation of the natural (unlabeled, typically biologically generated) version of the analyte (see U.S. Pat. No. 7,632,686 "High Sensitivity Quantitation of Peptides by Mass Spectrometry"). In one embodiment, a SIS peptide or protein comprises a peptide sequence that has a structure that is chemically identical to that of the molecule for which it will serve as a standard, except that it has isotopic labels at one or more positions that alter its mass. Accordingly, an SIS is: i) recognized as equivalent to the analyte in a pre-analytical workflow, and is not appreciably differentially enriched or depleted compared to the analyte prior to mass spectrometric analysis, and ii) differs from the analyte in a manner that can be distinguished by a mass spectrometer, either through direct measurement of molecular mass or through mass measurement of fragments (e.g., through MS/MS analysis), or by another equivalent means. Stable isotope standards include peptides having non-material modifications of this sequence, such as a single amino acid substitution (as may occur in natural genetic polymorphisms), substitutions (including covalent conjugations of cysteine or other specific residues), or chemical modifications (including glycosylation, phosphorylation, and other well-known post-translational modifications) that do not materially affect enrichment or depletion compared to the analyte prior to mass spectrometric analysis. Advantageously, an SIS contains a level of substitution of each stable isotope (e.g., C, N, or H) at the specific site or sites within the peptide structure where the isotope(s) is/are incorporated (i.e., those sites that depart significantly from the natural unenriched isotope distribution) of >95%, >96%, >97%, or >98%.

The term "SISCAPA" means the method described in U.S. Pat. No. 7,632,686, and in *Mass Spectrometric Quantitation of Peptides and Proteins Using Stable Isotope Standards and Capture by Anti-Peptide Antibodies (SISCAPA)* (*Journal Proteome Research* 3: 235-44 (2004).)

The term "small molecule" or "metabolite" means a multi-atom molecule other than proteins, peptides and DNA; the term can include but is not limited to amino acids, steroid and other small hormones, metabolic intermediate compounds, drugs, drug metabolites, toxicants and their metabolites, and fragments of larger biomolecules.

The term "stable isotope" means an isotope of an element naturally occurring or capable of substitution in proteins or peptides that is stable (does not decay by radioactive mechanisms) over a period of a day or more. The primary examples of interest in the context of the methods described herein are C, N, H, and O, of which the most commonly used are $^{13}$C, $^{15}$N, $^{2}$H, and $^{18}$O.

The term "standardized sample" means a protein or peptide sample to which one or more stable isotope labeled version(s) of one or more peptide or protein analytes have been added at known levels corresponding to test evaluation thresholds to serve as an internal standard or standards.

Hematocrit

Hematocrit (Hct) is a measure of the amount of space (volume) that red blood cells ("RBC") take up in the blood. The value is given as a percentage of red blood cells in a volume of blood. For example, a hematocrit of 38 means that 38% of the blood's volume is made of red blood cells. Hematocrit is also known as packed cell volume (PCV) or erythrocyte volume fraction (EVF). Normal values are about 45% for men, and 40% for women. The packed cell volume (PCV) can be determined by centrifuging heparinized blood in a capillary tube (also known as a microhematocrit tube) at 10,000 RPM for five minutes. This separates the blood into layers. The volume of packed red blood cells divided by the total volume of the blood sample gives the PCV. Because a tube is used, this can be calculated by measuring the lengths of the layers. With modern lab equipment, the hematocrit is calculated by an automated analyzer and not directly measured. It is determined by multiplying the red cell count by the mean cell volume. The hematocrit is slightly more accurate as the PCV includes small amounts of blood plasma trapped between the red cells.

It is well known that hematocrit values are affected by a number of factors, some of which can produce rapid changes. For example, posture can change hematocrit by up to 8% in a period of 10 minutes. (Ahlgrim et al., *Int J Lab Hematol* 32, 506-511, (2010); Touitou et al., *Clin. Chem.* 32, 801-804.)

Influence of Hematocrit on the Interpretation of Measured Values of Diagnostic Proteins in Blood Numerous clinical tests involve measurement of a specific protein in a sample of blood, serum or plasma, for example the measurement of C-reactive protein (CRP) as an indicator of cardiovascular risk. In most cases such measurements are carried out using plasma or serum, which are respectively the liquid component of blood after the cells have been removed and the blood is either prevented from clotting (plasma) or is allowed to clot (serum is obtained after the clot is removed). Hence a measurement of CRP in plasma yields a concentration value (for example 1.5 mg/L) that differs from its concentration in whole blood, in which the plasma may represent only 50% of the volume (the rest being made up of RBC, and smaller contribution of white blood cells ("WBC") and platelets). In this case the concentration in whole blood can be calculated from a plasma or serum measurement (or vice versa) if: i) there is little or no CRP in the non-plasma components (the cells); and ii) the actual hematocrit value (which can vary from 30-60% in normal patients and more widely in abnormal patients) in the sample is known.

The first assumption can be justified if it has been established that the majority of the protein being measured is found in the plasma (or serum) and not in the cells, as is the case for most (but not all) protein biomarkers measured clinically in plasma. Dealing effectively with the second factor involves actual measurement or estimation of the hematocrit in the individual sample. Conventional methods of hematocrit measurement (such as centrifugal sedimentation of the RBC in a capillary filled with whole blood) require whole blood in liquid form with the RBC intact. It is a challenge, however, to calculate an equivalent plasma (or serum) concentration from a measurement made on a whole blood sample when the true hematocrit cannot be measured (for example in a dried blood spot sample in which the blood cells are broken open and their contents released). The methods described herein address this problem by making it possible to calculate an estimate of hematocrit from protein assay measurements.

The Problem of Varying Hematocrit in Regard to the Interpretation of Diagnostic Tests on Dried Blood Spots A drop of fresh whole blood obtained by finger-prick (or by venipuncture) can be placed on filter paper, where it spreads into a circle, and then dried to form a stable specimen: a "dried blood spot" or DBS. DBS have been used for many years as a means of collecting neonatal "heel-stick' blood samples for use in screening for inborn errors of metabolism and more recently have been adopted for use in pharmaceutical trials and clinical testing because they are stable (in many cases for years) and easy to transport and store compared to blood, serum or plasma (which must typically be stored long term at −80 C).

When whole blood dries, the cells typically break and release most or all of their contents to mix with the surrounding plasma. Microscopic examination reveals that the resulting dried material is a translucent red matrix congealed upon and among the fibers of the filter paper used as DBS substrate. Despite the uniformity of the filter paper, the size of the spot produced for a given volume of blood dropped on the paper is not exactly reproducible. This variation results in variation in the amount of blood per area of the paper, and thus variation in the amount of blood obtained when a specified area of the paper is sampled, either by punching out an area for analysis in a separate container, by flow of liquid through a defined area clamped in an elution device, or by direct surface sampling. Hence both these sources of variation (mixing of compartments and variation in blood per area) contribute to uncertainty in the estimation of a biomarker molecule in a specific compartment. (e.g., plasma) of the original sample.

One approach to solving the compartment mixing problem is to separate the plasma from the cells before or as part of the process of preparing a dried spot: in this case yielding a dried plasma spot. This can be done in one of a number of special devices (e.g., the Advance DX100 card, Advance Dx, Inc. (Chicago, Ill.)) or the device described in U.S. Pat. Nos. 6,106,732 and 6,258,045 made for the purpose. The disadvantages of this approach include the higher cost of such multicomponent devices compared to filter paper, greater requirement for user proficiency, and variable yield of serum or plasma.

Similarly, devices and methods have been developed to minimize the variation in blood volume obtained when sampling conventional DBS. In one approach, a bounded area of filter paper is wetted with a measured volume of blood, which is then dried (Youhnovski et al., *Rapid Commun Mass Spectrom* 25:2951-2958). By analyzing the whole of this bounded filter paper area, the equivalent of a fixed, measured blood volume is obtained. In another version of this approach a fixed blood volume, typically measured by filling a capillary tube with blood, is applied to the paper forming a circular area spot, all of which is used in the analysis (by punching or otherwise sampling an area larger than the applied spot). The disadvantages of this approach are the need for a separate measuring step in the blood collection, and in applicable cases the need for a more elaborate perforated or otherwise shaped piece of paper.

The "Complete Blood Count" or "CBC"

A complete blood count (CBC) is defined as a diagnostic test that counts the numbers of several types of blood cells in a fixed quantity of blood. A CBC typically is used to evaluate a patient's overall health and to detect a wide range of disorders, including anemia, infection and leukemia. A complete blood count test measures several components and features of blood, including: RBC, which carry oxygen; WBC cells, which fight infection; and platelets, which help with blood clotting.

Additional valuable information is obtained by further analysis of subsets of WBC cells in a so-called "differential" count. The major types of WBC are neutrophils, lymphocytes, monocytes, eosinophils, and basophils. Immature neutrophils, called band neutrophils, are also part of this test. The numbers of each one of these types of white blood cells give important information about the immune system. Too many or too few of the different types of white blood cells can help find an infection, an allergic or toxic reaction to medicines or chemicals, and many conditions, such as leukemia.

Blood leukocytes, and particularly subtypes of lymphocytes, can be "stained" with fluorescently labeled antibodies specific for certain functional lymphocyte subsets, and these cells counted using flow cytometers. In general these antibodies recognize well-characterized protein molecules on the surfaces of the lymphocytes called "CD" antigens (each of which is given a number; e.g., CD45). A particular type of cell may, for example, be characterized as a CD4+ CD25+ regulatory T-cell, indicating that this cell population has both CD4 and CD25 molecules on its surface. It is possible, using flow cytometry, to measure the average number of molecules of a CD antigen on the surface of a specific type of cell (Bikoue et al. *Clin Immunol. and Immunopath.* 84, 56-64 (1997)). Thus it can be determined that a type of lymphocyte has on average 47,000 molecules of CD4 antigen per cell, which, when multiplied by the number of such cells per $mm^3$ of blood, allows computation of the number of molecules, and thus the number of moles, of the CD antigen protein in any volume of blood. Some but not all of these CD antigens occur primarily on a single type of cell and can thus be used to carry out this inverse calculation: i.e., a measurement of the amount of such a cell-type specific protein in a sample (in molecules), can be divided by the known average number of molecules of this protein per cell to yield the number of such cells in the sample.

In each of these tests, with the exception of hematocrit (detailed below) and hemoglobin, the result is based upon actually counting cells or particles, either using a microscope or a specialized (usually automated) instrument. Such counts are thus measures of cell or particle number rather than the aggregate physical mass or total volume of the specific type of cell or particles being counted. This distinction is important in the interpretation of results obtained by measurement (as disclosed in the invention) of protein or other molecular constituents of the cells or particles being counted.

Multiplex Protein Assays Using Mass Spectrometry

Almost all protein assays used clinically are tests for a single protein, requiring multiple sample aliquots (and progressively increasing cost) for the measurement of multiple proteins. This has discouraged normalization or calibration of clinical analyte measurements using measurements of additional protein analytes that may not be clinically required. Thus, in the case of proteins measured clinically in plasma, current practice does not make use of ratio measurements involving normalizing proteins either plasma (e.g., HSA or total plasma protein) or in other compartments. In the field of proteomics, multiple proteins are measured routinely because the technologies (typically mass spectrometry) make this easy to do. Until recently, however, proteomics has not been concerned with high precision measurements of the kind required in clinical use, and has not considered the partition of complex proteome samples into the contributions of different compartments—it has been the preferred approach to isolate such compartments first and then carry out proteomic analysis.

The SISCAPA Method

Recently it has become possible to measure proteins accurately in multiplex panels using mass spectrometry—a direct detection approach in contrast to the indirect detection in immunoassays based on antibodies. The power of this mass spectrometric approach is further increased by means of sample preparation steps to improve its sensitivity and throughput. A prominent means of such improvement is the SISCAPA technology. SISCAPA assays combine affinity enrichment of specific peptides with quantitative measurement of those peptides by mass spectrometry. In order to detect and quantitatively measure protein analytes, the SISCAPA technology makes use of anti-peptide antibodies (or any other binding entity that can reversibly bind a specific peptide sequence of about 4-20 residues) to capture specific peptides from a highly complex mixture of peptides, such as that arising, for example, from the specific cleavage of a protein mixture (like human serum or a tissue lysate) by a proteolytic enzyme such as trypsin or a chemical reagent such as cyanogen bromide. By capturing a specific peptide through binding to an antibody (the antibody being typically coupled to a solid support either before or after peptide binding), followed by washing of the antibody:peptide complex to remove unbound peptides, and finally elution of the bound peptide into a small volume, the SISCAPA technology makes it possible to enrich specific peptides that may be present at low concentrations in the whole digest, and that are therefore undetectable in simple mass spectrometry (MS) or liquid chromatography-MS (LC/MS) systems against the background of more abundant peptides present in the mixture. SISCAPA also provides a sample that is much less complex, and therefore exhibits lesser 'matrix effects' and fewer analytical interferences, than the starting digest, which in turn enables use of shorter (or no) additional separation processes to introduce samples into a suitable mass spectrometer.

The enrichment step in SISCAPA is intended to capture peptides of high, medium or low abundance and present them for MS analysis; it therefore discards information as to the relative abundance of a peptide in the stinting mixture in order to boost detection sensitivity. This abundance information can be recovered, however, through the use of isotope dilution methods: the SISCAPA technology makes use of such methods (e.g., by using stable isotope labeled versions of target peptides) in combination with specific peptide enrichment, to provide a method for quantitative analysis of peptides, including low-abundance peptides.

The approach to standardization in SISCAPA is to create a version of the peptide to be measured which incorporates one or more stable isotopes of mass different from the predominant natural isotope, thus, forming a labeled peptide variant that is chemically identical (or nearly-identical) to the natural peptide present in the mixture, but which is nevertheless distinguishable by a mass spectrometer because of its altered peptide mass due to the isotopic label(s). The isotopic peptide variant (a Stable Isotope-labeled Standard, or MS) is used as an internal standard, added to the sample peptide mixture at a known concentration before enrichment by antibody capture. The antibody thus captures and enriches both the natural and the labeled peptide together (having no differential affinity for either since they are chemically the same) according to their relative abundances in the sample. Since the labeled peptide is added at a known concentration, the ratio between the amounts of the natural and labeled forms detected by the final MS analysis allows the concentration of the natural peptide in the sample mixture to be calculated. Thus, the SISCAPA technology makes it possible to measure the quantity of a peptide of low abundance in a complex mixture and, since the peptide is typically produced by quantitative (complete) cleavage of sample proteins, the abundance of the parent protein in the mixture of proteins can be deduced. The SISCAPA technology can be multiplexed to cover multiple peptides measured in parallel, and can be automated through computer control to afford a general system for protein measurement.

An alternative to using SIS peptides is to use multiple copies of SIS peptides arranged as a linear polypeptide strand known as polySIS peptides. PolySIS peptides have been described, for example, in U.S. patent application Ser. No. 11/147,397 and may be prepared chemically, in vitro or in vivo using the same techniques used for SIS peptides. PolySIS peptides may also be prepared in "extended SIS" form and coupled to a carrier in the same fashion that SIS peptides or extended SIS peptides are attached.

The foregoing disclosure outlines to number of embodiments in terms of the SISCAPA method and associated quantitative mass spectrometry methods, and therefore represents one set of embodiments that may be employed in the application of the present technology. It will be appreciated that the methods and compositions disclosed herein are not limited to the SISCAPA method, but may be applied to other methods that employ internal peptide standards and the like.

Embodiments

Determination of Hematocrit in a Dried Blood Sample and Application to Normalize Protein Test Results In this example a set of proteins is selected that are specific, or nearly specific, to two or more compartments in a sample (i.e., Compartment Specific Molecules, or CSMs). Measurement of these CSM proteins can be accomplished by a variety of methods, including immunoassay, but preferably is accomplished using mass spectrometry (MS) to measure the relative amounts of monitor peptides derived from the CSM's by proteolytic digestion of the sample to yield a digest. Such monitor peptides are typically selected from peptides unique to a specific CSM protein so that the monitor peptide occurs in the sample in fixed molar proportion (usually 1:1) with the CSM protein. These assays advantageously can use the SISCAPA methodology.

One instance of this embodiment involves estimating the composition of whole human blood, and particularly the hematocrit (Hct), from measurements of proteins present in a dried blood spot sample. Liquid blood obtained from a human being contains RBC, a variety of WBC (leukocytes), platelets, and plasma proteins, as well as additional minor components, each constituting a "compartment" of the mixed sample. Once this mixture is dried on filter paper, the cells are broken and the contents of the various compartments at least partially mixed. The relative concentration of a specific plasma protein in proportion to the total protein in the sample is thereby reduced, compared to the situation in separated plasma, by 'dilution' with RBC and other proteins. The amount of RBC proteins likewise is diluted by combination with plasma proteins. In general the amounts of other compartments in blood are small in comparison to the amounts of plasma and RBC.

It is useful to know the volume proportion of plasma, RBC, etc., in the specific blood sample, in order to correct a measurement of a plasma protein carried out on whole blood to yield an estimate of the amount of that plasma protein if it had been measured in separated plasma (as is typical practice in clinical laboratory tests for many protein biomarkers). The proportion of liquid blood corresponding to RBC can be measured (the classical hematocrit measurement), and each WBC type measured (usually by counting), but this is typically not done on blood samples prior to collection of a dried blood spot, and hence this information on the relative amount of RBC, WBC and plasma protein in a sample is usually lost upon drying.

If, however, one or more proteins characteristic of each compartment (i.e. CSM) is measured in an aliquot of the mixed sample, then the relative volume amounts of each compartment can be estimated using reasonable assumptions as to the normal concentration of each protein in its native compartment. For example, the normal concentration of albumin (HSA) in plasma is 44 mg/ml (34-54 mg/ml reference range), and the normal concentration of hemoglobin (Hb, characteristic of the RBC compartment) in packed RBC is 340 mg/ml (320 to 360 mg/ml), while hematocrit (Hct) averages 45% in men and 40% in women. The ratio (Rw) between the weight per volume concentrations of HSA and Hb in adult male blood with normal hematocrit is thus $((1-45\%) \times 44 \text{ mg/ml})/(45\% \times 340 \text{ mg/ml}) = 24.2/153 = 0.158$. If this ratio is measured experimentally in a sample, and the plasma HSA and RBC Hb concentrations assumed to be normal, then the hematocrit can be estimated from the following equation:

$$Hct = 1/(1+(Rw*340/44)) = 1/(1+7.7*Rw).$$

Given the molecular weights of HSA (69,367) and a hemoglobin dimer (31,256; the molar unit of Hb), the same calculation can be done on a molar basis. Here the normal concentration of HSA in plasma is $0.634 \times 10^{-3}$ mol/L ($0.49 \times 1.0^{-3}$ to $0.78 \times 10^{-3}$ mol/L reference range), and the normal concentration of Hb in packed RBC is $10.8 \times 10^{-3}$ mol/L ($10.2 \times 10^{-3}$ to $11.5 \times 10^{-3}$ mol/L). The Hb measurement can be accomplished by quantitating either the Hb alpha chain, the Hb beta chain, or both, since the alpha and beta chains are present in near-equal stoichiometric amounts. The ratio (Rm) between the molar concentrations of HSA and Hb in blood with normal hematocrit is thus $((1-45\%) \times 0.634 \times 10^{-3} \text{ mol/L})/(45\% \times 10.8 \times 10^{-3} \text{ mmol/L}) = 0.071$. If this ratio is measured experimentally in a sample, and the plasma HSA and RBC Hb concentrations assumed to be normal, then the hematocrit can be estimated from the following equation:

$$Hct = 1/(1+(Rm*10.8/0.634)) = 1/(1+17*Rm).$$

Use of a molar basis, rather than a weight basis, for such calculations is more appropriate when the CSM proteins are quantitated by mass spectrometry methods yielding values in femtomoles.

Measurements of the amounts of HSA and Hb can be obtained by measuring the amounts of one or more monitor peptides of HSA (for example Seq ID's 1-5; Table 1) and one or more monitor peptides of Hb (for example Seq ID's 21-24 from the alpha chain and/or Seq ID's 25-29 from the beta chain) in relation to stable isotope labeled (SIS) version of the monitor peptides added to the digest in known amounts prior to MS analysis. In the case of monitor peptides whose yield in digestion is near 100% (i.e., molar equivalent to the parent protein), the measured peptide quantities can be used directly as described above to estimate the Hct. In a case where one or more peptides is not generated with equal (or near 100%) efficiency in the process of digestion, a conversion factor correcting for digestion yield may be applied. Such digestion correction factors, relating moles of monitor peptide produced by digestion to moles of parent protein in the sample, can be obtained by calibration of the measurements with calibrator samples containing known amounts of the parent proteins.

TABLE 1

| Compartment-specific protein | UniProt | Seq ID | Example Monitor peptide(s) |
|---|---|---|---|
| Albumin (HSA) | P02768 | 1 | LVNEVTEFAK |
| | | 2 | ALVLIAFAQYLQQCPFEDHVK |
| | | 3 | YLYEIAR |
| | | 4 | DVFLGMFLYEYAR |
| | | 5 | FSALEVDETYVPK |
| Ig lambda LC | | 6 | YAASSYLSLTPEQWK |
| | | 7 | AGVETTTPSK |
| | | 8 | AAPSVTLFPPSSEELQANK |

TABLE 1-continued

| Compartment-specific protein | UniProt | Seq ID | Example Monitor peptide(s) |
|---|---|---|---|
| Ig kappa LC | | 9 | DSTYSLSSTLTLSK |
| | | 10 | TVAAPSVFIFPPSDEQLK |
| Transferrin | P02787 | 11 | EDPQTFYYAVAVVK |
| | | 12 | QQQHLFGSNVTDCSGNECLFR |
| | | 13 | MYLGYEYVTAIR |
| | | 14 | IECVSAETTEDCIAK |
| | | 15 | LCMGSGLNLCEPNNK |
| alpha-2-macroglobulin | P01023 | 16 | NEDSLVFVQTDK |
| | | 17 | SSGSLLNNAIK |
| | | 18 | NQGNTWLTAFVLK |
| | | 19 | VGFYESDVMGR |
| | | 20 | AIGYLNIGYQR |
| Hb alpha | P69905 | 21 | AGEYGAEALER |
| | | 22 | LASVSTVLTSK |
| | | 23 | ASVSTVLTSK |
| | | 24 | GEYGAEALER |
| Hb beta | P68871 | 25 | VHLTPEEK |
| | | 26 | LVVYPWTQR |
| | | 27 | VDEVGGEALGR |
| | | 28 | GDLSTPDAVMGNPK |
| | | 29 | STPDAVMGNPK |
| Carbonic anhydrase 1 | P00915 | 30 | GGPFSDSYR |
| | | 31 | GLAVIGVLMK |
| | | 32 | ASPDWGYDDK |
| | | 33 | DGLAVIGVLMK |
| | | 34 | SISVSSEQLAQFR |
| CD45 | P08575 | 35 | TLILDVPPGVEK |
| | | 36 | FQCGNMIFDNK |
| | | 37 | LFLAEFQSIPR |
| | | 38 | DETVDDFWR |
| | | 39 | DLQYSTDYTFK |
| L-plastin | P13796 | 40 | YAFVNWINK |
| | | 41 | VYALPEDLVEVNPK |
| | | 42 | LSPEELLLR |
| | | 43 | FSLVGIGGQDLNEGNR |
| | | 44 | GSVSDEEMMELR |
| CD19 | P15391 | 45 | NPDGPDPAWGGGGR |
| | | 46 | GTSDGPTQQLTWSR |
| | | 47 | GNVLSLPTPTSGLGR |
| | | 48 | DMWVMETGLLLPR |
| | | 49 | NPSSDVQADGALGSR |
| CD20 | P11836 | 50 | NSVNGTFPAEPMK |
| | | 51 | AHTPYINIYNCEPANPSEK |
| | | 52 | SNIVLLSAEEK |
| CD38 | P28907 | 53 | IKDLAHQFTQVQR |
| | | 54 | VQTLEAWVIHGGR |
| | | 55 | DLAHQFTQVQR |
| | | 56 | DLCQDPTIK |
| | | 57 | INYQSCPDWR |
| CD22 | P20273 | 58 | VSMSPGDQVMEGK |
| | | 59 | YEWKPHGAWEEPSLGVLK |
| | | 60 | YCCQVSNDVGPGR |
| | | 61 | EGDTVTLSCNYNSSNPSVTR |
| | | 62 | SPLSTLTVYYSPETIGR |
| CD3 | P07766 | 63 | DLYSGLNQR |
| | | 64 | GSKPEDANFYLYLR |
| | | 65 | QDGNEEMGGITQTPYK |
| | | 66 | EFSELEQSGYYVCYPR |
| | | 67 | ERPPPVPNPDYEPIR |
| CD58 | P13591 | 68 | FIVLSNNYLQIR |
| | | 69 | LEGQMGEDGNSIK |
| | | 70 | GLGEISAASEFK |
| | | 71 | LPSGSDHVMLK |
| | | 72 | AGEQDATIHLK |

TABLE 1-continued

| Compartment-specific protein | UniProt | Seq ID | Example Monitor peptide(s) |
|---|---|---|---|
| CD4 | P01730 | 73 | SLWDQGNFPLIIK |
| | | 74 | LTGSGELWWQAER |
| | | 75 | IDIVVLAFQK |
| | | 76 | ILGNQGSFLTK |
| | | 77 | EGEQVEFSFPLAFTVEK |
| CD64 | P12314 | 78 | VFTEGEPLALR |
| | | 79 | VISSLQEDR |
| | | 80 | LVYNVLYYR |
| CD14 | P08571 | 81 | TTPEPCELDDEDFR |
| | | 82 | ATVNPSAPR |
| | | 83 | TSLDLSDNPGLGER |
| | | 84 | SWLAELQQWLK |
| | | 85 | TPEPCELDDEDFR |
| CD11a | P20701 | 86 | AGYLGYTVTWLPSR |
| | | 87 | TSLLASGAPR |
| | | 86 | GNVDLVFLFDGSMSLQPDEFQK |
| | | 89 | DWAGGFLDLK |
| | | 90 | IGNEPLTPEVR |
| Myeloperoxidase (MPO) | P05164 | 91 | DYLPLVLGPTAMR |
| | | 92 | IANVFINAFR |
| | | 93 | VVLEGGIDPILR |
| | | 94 | IGLDLPALNMQR |
| | | 95 | FCGLPQPETVGQLGTVLR |
| Neutrophil elastase | P08246 | 96 | NWIDSIIQR |
| | | 97 | AQFVNWIDSIIQR |
| | | 98 | LAMGWGLLGR |
| | | 99 | NANVQVAQLPAQGR |
| Defensin, alpha 1 | P59665 | 100 | YGTCIYQGR |
| | | 101 | IPACIAGER |
| | | 102 | DIPEVVVSLAWDESLAPK |
| Matrixmetallopeptidase 8 (neutrophil collagenase) | P22894 | 103 | NYTPQLSEAEVER |
| | | 104 | ISQGEADINIAFYQR |
| | | 105 | YYAFDLIAQR |
| | | 106 | LTFDAITTIR |
| | | 107 | DAFELWSVASPLIFTR |
| PRG2 | P13727 | 108 | IQCSVSALNQGQVWIGGR |
| | | 109 | SLQTFSQAWFTCR |
| | | 110 | GNLVSIHNFNINYR |
| | | 111 | VVGIPGCQTCR |
| | | 112 | SALNQGQVWIGGR |
| PF-4 | P02776 | 113 | FASAEAEEDGDLQCLCVK |
| | | 114 | HITSLEVIK |
| | | 115 | AGPHCPTAQLIATLK |
| | | 116 | ICLDLQAPLYK |
| | | 117 | TTSQVRPR |
| CD61 (integrin beta chain beta 3) | P05106 | 118 | IGDTVSFSIEAK |
| | | 119 | GSGDSSQVTQVSPQR |
| | | 120 | YCECDDFSCVR |
| | | 121 | DDLWSIQNLGTK |
| | | 122 | VLTLTDQVTR |
| pro-platelet basic protein (chemokine (C-X-C motif) ligand 7) | P02775 | 123 | NIQSLEVIGK |
| | | 124 | SLDSDLYAELR |
| | | 125 | NQVEVIATLK |
| | | 126 | GTHCNQVEVIATLK |
| | | 127 | ICLDPDAPR |
| Integrin, alpha 2b (platelet glycoprotein IIb of IIb/IIIa complex, antigen CD41) | P08514 | 128 | GQVLVFLGQSEGLR |
| | | 129 | IVLLDVPVR |
| | | 130 | NVGSQTLQTFK |
| | | 131 | GEAQVWTQLLR |
| | | 132 | ALSNVEGFER |
| Selectin P (granule membrane protein 140 kDa, antigen CD62) | P16109 | 133 | YTDLVAIQNK |
| | | 134 | WTDSPPMCEAIK |
| | | 135 | LEGPNNVECTTSGR |

TABLE 1-continued

| Compartment-specific protein | UniProt | Seq ID | Example Monitor peptide(s) |
|---|---|---|---|
| | | 136 | NNEDCVEIYIK |
| | | 137 | YSSYYWIGIR |

The estimated Hct value for a blood sample that was subsequently prepared as a dried blood spot is a very useful piece of information. Using the Hct, one skilled in the art can convert between quantitative measurements of a protein in DBS on the one hand, and in plasma or serum on the other, provided that the protein is known to be located in either the plasma or RBC compartments of the blood. For a protein that is normally present in the plasma compartment, the conversion factor applied (by multiplication) to a measurement of a protein in DBS can be estimated as 1/(1−Hct). This factor represents the greater concentration of the protein in a volume of plasma compared to the same volume of whole blood. Similarly a measurement in a DBS sample of a protein present in RBC can be used to estimate the amount in the RBC compartment by multiplying by 1/Hct, the conversion factor assuming equal volumes of packed RBC and whole blood are being compared.

On average, RSA represents approximately 50% of the total protein content of human plasma, is not produced in blood cells and is thus a good choice for a plasma CSM. However HSA can vary somewhat in disease states because it behaves as a negative acute phase reactant (its concentration declines slightly in response to infectious disease and inflammation). A more robust approach to measuring the plasma compartment includes additional high abundance plasma proteins in an aggregate measure of the plasma compartment. The second highest abundance protein class in plasma by mass (typically representing 13% of plasma protein) is the immunoglobulins (Ig's), which incorporate a variety of heavy chain types and isotypes, and two light chain forms (kappa and lambda) in a stochiometric relationship with the heavy chains. A variety of means can be used to measure the higher abundance Ig chains, but a simple approach applied in the present methods is to measure one or monitor peptides characteristic of, and therefore stoichiometrically representing, all kappa light chains (for example Seq ID's 9 and 10) and one or more monitor peptides characteristic of, and therefore stoichiometrically representing, all lambda light chains (for example Seq ID's 6-8).

The sum of the molar amounts of kappa and lambda light chains can be used as an estimate of the molar amount of the average Ig heavy+light chain unit (having an average molecular weight of approximately 75,000 daltons), thereby providing an estimate of the amount of Ig in the sample. Similarly, a further improved estimate of the amount of plasma protein can be obtained by adding measurements of the amounts of transferrin (the third most abundant protein in plasma at 3%) using, for example, Seq ID's 1.1-15 as monitor peptides, and alpha-2-macroglobulin (the fourth most abundant protein in plasma at 3%) using, for example, Seq ID's 16-20 as monitor peptides. By combining measured amounts of HSA (50%), Ig (13%), transferrin (3%) and alpha-2-macroglobulin (3%), which together account for approximately 70% of the protein content of normal human plasma, one can obtain an improved estimate of the total amount of protein in human plasma and, thereby, using this more representative aggregate estimate in place of the HSA measurement alone, obtain a better estimate of the Hct.

In similar fashion, the proportions of other mixture compartments such as white blood cells (WBC), including subcompartments such as lymphocytes (and their subtypes T and B cells, etc), as well as neutrophils and monocytes, can be measured.

Measurement of multiple proteins in a complex sample is advantageously done as part of a single multiplex panel test, rather than as a series of separate determinations requiring multiple aliquots of the sample.

Determination of Total Amount of Blood Material Contained in a Dried Blood Sample In this second example, the weight or molar amounts of plasma and RBC compartments are measured as in the first example above, and the volumes of the two compartments estimated using previously established average concentrations of the two compartments. Thus using the normal concentration of HSA in plasma ($0.634 \times 10^{-3}$ mol/L) and the normal concentration of Hb in packed RBC ($10.8 \times 10^{-3}$ mol/L), the measured molar amounts of these CSM can be converted to the physical volumes of the respective compartments (e.g., the moles of HSA divided by the normal concentration of HSA in plasma in mol/L yields the volume of plasma in liters; and similarly for Hb in packed RBC). Adding the plasma volume and RBC volume together provides an estimate of the total volume of blood in the sample, since the other compartments of blood (leukocytes and platelets) have negligible volume in comparison to plasma and RBC.

This provides a means of determining the actual volume of liquid blood that was dried in an individual dried blood spot sample independent of its area, weight or dried volume. The methods therefore provide a way of normalizing measurements of protein and other biomarkers (different from the CSMs) in dried blood spots to remove the effect of varying sample volume.

Determination of Blood Cell Counts from Protein Amounts in a Dried Blood Sample

In a third example, the average CSM copy number (number of molecules) per cell is used to estimate the number of cells per microliter in a compartment of the sample. Given the number of molecules of a CSM per cell for a given compartment (for example 10,000 copies of a lymphocyte specific surface receptor protein per cell), then the number of such molecules detected by measuring its monitor peptide(s) in a given volume of sample digest allows calculation of the number of cells from which the peptide was derived (by dividing the number of molecules detected by the number of molecules per cell) and, hence, the number of such cells in the sample volume digested. In many ways this information is more directly useful than a measurement of the compartment volume, especially for white cells and platelets.

Ideally the CSM's selected have a direct functional association with the compartment they are used to measure, and contribute to a unique function that defines or helps to define the compartment itself. Examples include hemoglobin (whose oxygen-carrying function is the primary function of the red cells in which it resides), or T-lymphocytes, which carry T-cell receptors enabling their function in the immune system. It is clear that definable compartments can be subdivided (e.g., the lymphocytes can be divied into T and B, and further into T classes etc). In some cases two definable compartments can share some components (e.g., when compartments are defined by multiple surface protein markers such as CD markers, there can be cells that have marker A but not B, B but not A, neither A nor B, or A and B—compartment bearing marker B is therefore further dividable into at least two subcompartments that either have or do not have A).

In most clinically-relevant compartments of blood, past research has indicated proteins that are specific for that compartment or nearly so, likewise in solid tissues, there are numerous proteins known to occur predominantly in a defined subset of the cells present—in many cases these proteins are revealed by specific antibodies using the methods of immunohistochemistry widely used in clinical pathology.

A series of known compartment markers can be employed in this manner, examples of which are shown in Table 2.

TABLE 2

| Compartment | | | | Compartment-specific protein (CSM) | UniProt |
|---|---|---|---|---|---|
| RBC | | | | Hb alpha | P69905 |
| | | | | Hb beta | P68871 |
| | | | | Carbonic anhydrase 1 | P00915 |
| Leukocytes | | | | CD45 | P08575 |
| | | | | L-plastin | P13796 |
| | Lymphocytes | B-cells | | CD19 | P15391 |
| | | | | CD20 | P11836 |
| | | | | CD38 | P28907 |
| | | | | CD22 | P20273 |
| | | T-cells | | CD3 | P07766 |
| | | | NK | CD56 | P13591 |
| | | | Helper T | CD4 | P01730 |
| | Monocytes | | | CD64 | P12314 |
| | | | | CD14 | P08571 |
| | | | | CD11a | P20701 |
| | Neutrophilis | | | Myeloperoxidase (MPO) | P05164 |
| | Neutrophilis | | | Neutrophil elastase | P08246 |
| | | | | Defensin, alpha 1 | P59665 |
| | | | | MMP8 | P22894 |
| | Eosinophils | | | PRG2 | P13727 |
| Platelets | | | | PF-4 | P02776 |
| | | | | CD61 | P05106 |
| | | | | Platelet basic protein | P02775 |
| | | | | CD41 | P08514 |
| | | | | CD62 | P16109 |

The CSM's of Table 2 measured, for example, using one or more of the monitor peptides of Table 1, can be used to assess the relative amounts of the respective cellular compartments in a blood sample. Thus, measurement of the amount of CD45 or L-plastin in a sample can provide an estimate of the relative content of the leukocyte compartment when comparing different samples. Similarly, measurements of CD 19, 20, 22 or 38 can be used to estimate the B-lymphocyte compartment; CD3 to estimate total T-cells; CD56 the total amount of the NK ("natural killer") lymphocyte population; CD4 the total amount of the Helper T-cell population (important in monitoring HIV/AIDS treatment); CD 64, 14 or 11a in measuring the monocyte compartment; MPO, neutrophil elastase, MMP8 and defensin alpha 1 in measuring the neutrophil compartment; PRG2 in measuring the eosinophil compartment; and PF-4, CD41, CD61, CD62, and platelet basic protein in measuring the platelet compartment.

Such compartment measurements have diagnostic value in comparing samples even without a conversion to cell counts. Numerous other CSM's are described in the art and can be used to define these and other blood compartments. Since most cells, other than RBC, have a single diploid nucleus, a protein that is present in an amount stoichiometric with the nuclear DNA is likely to be proportional in amount to the number of nuclei, and thus the number of nucleated cells in which it occurs. Histone proteins, or others that form a regular part of the chromosomal structure are ideal, provided that they are specific to the desired compartment. In this sense the major histones, occurring in all nucleated cells, can be used to measure all the nucleated cells—the sum of lymphocyte, neutrophil, monocyte, and eosinophil compartments in blood. A person skilled in the art can use a variety of methods to predict or observe which monitor peptides are suited to measure CSM's in proteolytic digests of biological samples such as blood or other tissues.

Knowledge of the number of molecules of a CSM present on or in a typical cell of a given compartment (the "copy number" or molecules/cell) allows one to convert a molar measurement of a CSM in a sample to a measurement of the number of cells in the compartment of the sample. In the case of the widely used CD marker proteins, quantitative studies, often using fluoresence flow cytometry, have established normal copy number values, some examples of which are shown in Table 3. This data, together with the number of cells of the compartment in blood from normal individuals (here showing the values at the low end of the normal range), can be used to estimate the molar amount of the CSM in a volume of blood equivalent to a conventional dried blood spot punch sample (approximately 20 μL of blood).

For the CSM's shown in Table 3, the amount of the CSM in the sample ranges from 0.2 to 17 fmol, molar amounts which provide sufficient amounts of respective monitor peptides to allow quantitation using current mass spectrometer instruments.

| Compartment | | Compartment-specific protein | Copies per cell | Cells per 20 ul (low normal) | fmol per 20 ul (low normal) |
|---|---|---|---|---|---|
| Leukocytes | | CD45 | 100,000 | 100,000 | 17 |
| Lymphocytes | B-cells | CD19 | 27,000 | 4,968 | 0.2 |
| | | CD20 | 150,000 | 4,968 | 1.2 |
| | Helper T-cells | CD4 | 47,000 | 9,936 | 0.8 |
| Monocytes | | CD14 | 110,000 | 2,700 | 0.5 |
| | | CD11a | 58,000 | 2,700 | 0.3 |

The capability to convert CSM molar measurements to cell counts (in the case of clinically relevant cellular blood compartments) allows determination of complete blood counts, including differential counts, from a dried blood spot sample.

Determination of the Total Amount of Blood in Solid Tissue Sample

In a fourth example, CSM's are used to quantitate the amount of blood in a sample of a tissue, for example by measuring plasma and RBC CSM's, or the amount of infiltration of the tissue by specific blood cells such as lymphocytes and neutrophils.

Determination of CD4+ T-Cell Counts in a Dried Blood Sample

In a fifth example, the number of CD4+ lymphocytes in blood can be estimated from a dried blood spot sample by measuring the amount of the CD4 protein in the dissolved blood spot (containing a known blood volume) and dividing this by the prior determined amount of CD4 protein typically present on CD4+ cells, to yield the number of CD4 cells in the said blood volume.

The foregoing disclosure outlines a number of embodiments using quantitative MS to measure CSM's relevant to blood compartments, and therefore represents one set of embodiments that may be employed in the application of the present technology. It will be appreciated that the methods and compositions disclosed herein are not limited to blood, to MS, or the SISCAPA method, but may be applied to other situations in which multi-compartment biological samples are analyzed.

Example

An analytical procedure is applied to dried blood spot (DBS) samples prepared by: (i) placing a drop of blood on a Whatman 903 sample card, (ii) allowing it to dry in air at room temperature for 2 hours, and (iii) storing the card at 4° C., in a sealed plastic bag with a packet of desiccant until analysis. Immediately prior to beginning the analytical workflow, a disk 6 mm in diameter is punched from the red area of dried blood using a standard office hole punch, yielding a flat red disk of paper containing the dry equivalent of about 15-20 µl of whole blood. The 6 mm disk is placed in the bottom of a well of a flat bottomed 96-well polypropylene plate (e.g., Greiner model 655201), 20 µL of water is added to the well, and the plate is shaken in a circular motion on a plate shaker (e.g., VarioMag Teleshake Plate Shaker at 900 rpm) for 30 minutes at room temperature to redissolve the DBS proteins. In this process, most of the red color theme) is extracted into the liquid, leaving the 903 paper a slightly dingy off-white color.

Next, a tablet of dry reagents is added to the well and the plate is again shaken for 30 minutes to dissolve the reagents and denature the sample proteins. This tablet is previously prepared by drying a 33.8 µL droplet of a solution of 9.13M urea, 0.5M Tris HCl pH 8.1 and 0.05M tris(2-carboxyethyl)phosphine (TECP) on a plastic sheet in air. When added to the 20 µL liquid of the redissolved DBS proteins in the well, the resulting urea concentration upon dissolution of the tablet is ~9M, ensuring good protein denaturation, and the TCEP concentration is sufficient to reduce all disulfide bonds in the proteins. Following denaturation and disulfide reduction, 20 µl of a fresh solution of iodoacetamide (7.5 mg/ml in water) is added to the well and allowed to react for 30 min at room temperature in the dark.

Next, the sample is diluted with 230 µL of 0.25M Tris HCl pH 8.1 in water and mixed by shaking the plate, after which 20 µL of a solution of trypsin (3.66 mg/ml trypsin, 1 mM HCl in water) is added to initiate tryptic digestion of the sample proteins. The plate is placed in a 37 C incubator for 4 hours to carry out the proteolytic digestion step. Next, 20 µL of a solution of 0.11 mg/ml N-a-tosyl-L-lysine chloromethyl ketone (TLCK, a trypsin inhibitor) in 1 mM HCl in water is added to the sample and mixed, inhibiting trypsin activity. The resulting sample digest now contains tryptic peptides in a solution of approximately 1M urea.

The SISCAPA method is used to enrich and measure a series of target peptides to practice one embodiment of the invention. In this example four target peptides are measured: two CSM's to measure the relative sizes of the plasma and RBC compartments in the blood, allowing estimation of the hematocrit, and two clinical protein analytes whose values are to be corrected to plasma-equivalent values using the estimated hematocrit. The peptides are:

VHLTPEEK, a proteotypic tryptic peptide derived from the human Hb beta chain (CSM for red blood cells);
LVNEVTEFAK, a proteotypic tryptic peptide derived front human albumin (HSA; a CSM for plasma);
GFVEPDHYVVVGAQR, a proteotypic tryptic peptide derived from the soluble form of the human transferrin receptor (a protein analyte used clinically to monitor a patient's iron status); and
EDQYHYLLDR, a proteotypic tryptic peptide derived from human protein C inhibitor is protein analyte under investigation as a marker for recurrence of prostate cancer)

A stable isotope labeled version of each of the 4 target peptides (the "SIS", or "heavy" versions) is prepared by peptide synthesis, each incorporating a C-terminal K or R residue fully labeled with $^{15}N$ and $^{13}C$ isotopes to provide mass increments relative to the endogenous tryptic peptides of 8 or 10 amu respectively. The quantity of each peptide is assessed by amino acid analysis to allow preparation of stock solutions of know quantity (typically 1 mmol/µL in 30% acetonitrile, 0.1% formic acid in water). A SIS mixture containing 50 fmol/µL of each of these SIS peptides is prepared in water containing 0.3% 3-[(3-cholamidopropyl)dimethylammonio]-1-propanesulfonate (CHAPS) detergent, and 10 µL of this mix is added to the sample and mixed by shaking to provide 500 fmol of each labeled internal standard. Next 10 µL of a solution containing, in phosphate-buffered saline (PBS), 0.1 mg/ml of each of four rabbit monoclonal antibodies with high affinity for the four respective target antibodies is added and mixed. These antibodies were previously prepared and are designated clone 16-9 AFG-18 (binding VHLTPEEK), clone 79 SAT-1 (binding LVNEVTEPAK), clone 79-9 PPI-6d (binding GFVEPDHYVVVGAQR), and clone 58-4 PPI-4d binding EDQYHYLLDR. This addition places 1 µg of each of the antibodies in the digest.

Next an aliquot of 20 µl of protein G-coated magnetic beads (Life Technologies 2.8 µm Protein G Dynabeads), previously washed in PBS, is added and the digest shaken for one hour while the target peptides bind to the specific antibodies and the antibodies bind to the protein G beads. The magnetic beads are removed from the digest, washed twice in 150 µL 0.03% CHAPS in PBS and once in 150 µL 0.03% CHAPS in water, using an Agilent Technologies "Bravo" laboratory robot (protocol described in Agilent Technologies Application Note 5990-7360EN published Jan. 25, 2011 and available at https://www.chem.agilent-.com).

Finally the beads are moved to a 96-well plate where they are mixed with 20 µL of 5% acetic acid in water for 10 minutes to elute the bound peptides, after which the eluate is moved to a clean 96-well PCR plate.

Peptide samples in the resulting eluate plate are analyzed with a system consisting of a 6490 triple quadrupole mass spectrometer coupled to a 1290 Infinity UHPLC using a JetStream interface (Agilent). A 10 µL aliquot of each sample is separated on a 2.1 mm×50 mm Zorbax 300 SB-C8 column with a flow rate of 0.6 mL/min. The target peptides are separated using a 3-min gradient with 0.1% formic acid in water as solvent A and 90% acetonitrile in 0.1% formic acid in water as solvent B. From initial conditions of 11% B, a gradient was developed to 16% B at 1 min, 22% B at 1.5 min, 35% B at 1.85 min, 70% B at 1.9 min, then back to 11% B from 1.95 to 3 min for column re-equilibration. Source conditions included drying gas at 200° C., sheath gas at 250° C., and 11 L/min flow for both drying and sheath gases. Ions are isolated in Q1 using 1.2 fwhm resolution and in Q3 using 0.7 fwhm resolution.

The following 8 MRM precursor/product ion transitions (Table 4) are measured during appropriate segments of the LC gradient, peptide peaks at expected retention times (previously determined for each peptide) are integrated using Agilent Mass Hunter quantitative software, and the endogenous analyte peak areas (light MRM) are divided by the corresponding labeled internal standard (heavy, SIS) peak areas to obtain a peak area ratio. The peak area ratio is then multiplied by 500 fmol (the amount of heavy peptide added to the sample) to compute the amount of the endogenous analyte peptide in the sample. Additional transitions can optionally be measured to facilitate detection and rejection of potential interferences in MS quantitation.

TABLE 4

| Protein | Peptide | Precursor Ion | Product Ion |
|---------|---------|---------------|-------------|
| HbA1C | VHLTPEEK_light | 476.76 | 716.38 |
| HbA1C | VHLTPEEK*_heavy | 480.77 | 724.40 |
| HSA | LVNEVTEFAK*_light | 575.31 | 937.46 |
| HSA | LNNEVTEFAK*_heavy | 579.31 | 945.48 |
| PCI | EDQYHYLLDR_light | 451.20 | 490.30 |
| PCI | EDQYHYILLDR*_heavy | 454.50 | 495.30 |
| sTfR | GFVEPDHYVVVGAQR_light | 558.30 | 734.90 |
| sTrR | GFVEPDHYVVVGAQR*_heavy | 561.60 | 739.90 |

Using this procedure, a series of blood samples having different known hematocrit values is digested and analyzed, and the ratio between the measured Hb and HSA molar amounts is used, in relation to known hematocrit values of the samples, to produce a calibration curve. Using this curve, the measured ratio of Hb to HSA (fmol to fmol) can be used to estimate the hematocrit in other samples of blood digests, in which other protein biomarkers are measured in addition to Hb and HSA.

Figure 2:
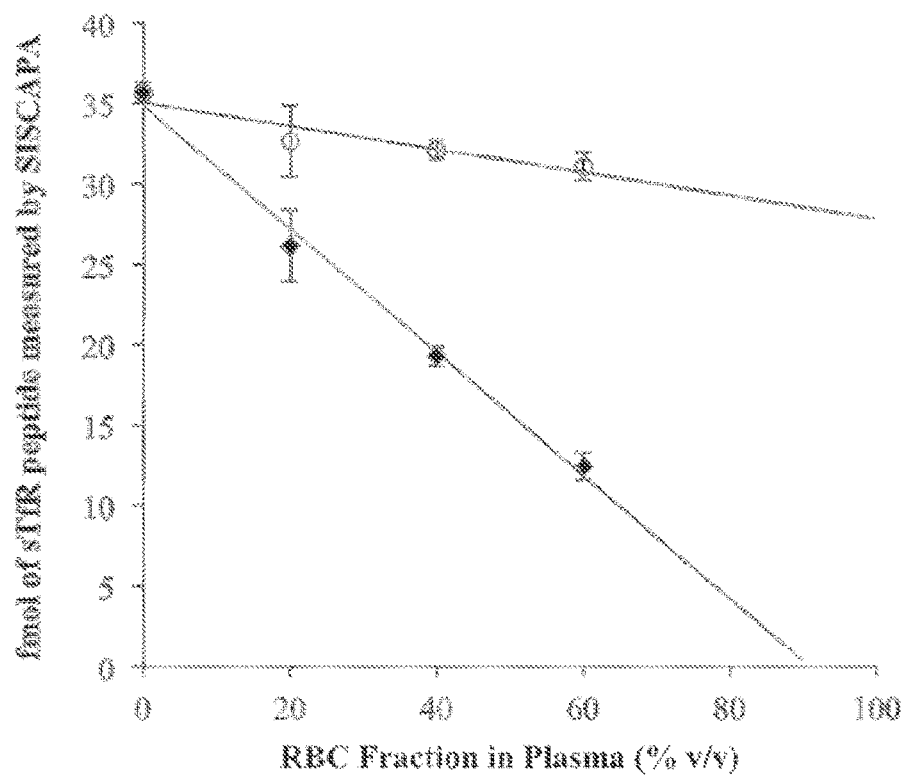
FIG. 2 shows a plot of the amount of soluble transferrin receptor detected in 4 aliquots of a blood sample adjusted to different hematocrit levels (0, 20, 40 and 60%), either before (filled symbols) or after (open symbols) normalization for hematocrit.

One such set of results is shown, in which 4 samples, made by combining aliquots of the same plasma with different amounts of RBC to produce different hematocrit values, is analyzed using the assay of Table 4. The measured levels (in fmol) of PCI and sTfR in the 4 samples are shown as solid symbols (with 1 standard deviation error bars from triplicate measurements) in FIG. 1 for PCI and FIG. 2 for sTfR. The measured amount of each protein in the samples declines as hematocrit increases, reflecting the decreasing amount of plasma in the blood as the volume fraction of RBC increases. However when the values measured in the different samples are corrected for the varying hematocrit of those samples, the values shown by open symbols are obtained. The corrected PCI and sTfR values demonstrate far less variation with changing hematocrit: the variation in PCI values between 0 and 60% hematocrit are only 11% as great after correction as before (sTfR variation after correction is reduced to 20% of the level without correction). Correction for measured hematocrit therefore allows much more accurate measurement of each protein in samples with any clinically-relevant (i.e., 25-55%) hematocrit level.

The invention claimed is:

1. A method for measuring the relative amounts of a first and a second compartment of a biological sample comprising:
   i) selecting a first monitor peptide that is proteotypic for a first protein whose amount in said sample is contributed predominantly by said first compartment,
   ii) selecting a second monitor peptide that is proteotypic for a second protein whose amount in said sample is contributed predominantly by said second compartment,
   iii) digesting said sample by means of a proteolytic process to produce a digest,
   iv) adding to said digest labeled versions of said first and second peptides, differing respectively from said first and second peptides by a mass increment, in known amounts,
   v) measuring the amounts of said first monitor peptide and said labeled version of said first monitor peptide using a mass spectrometer, dividing said measured amount of said first monitor peptide by said measured amount of said labeled version of said first monitor peptide to produce a first ratio, and multiplying said first ratio by the known amount of said labeled version of said first peptide to yield an amount of said first peptide in the digest,
   vi) measuring the amounts of said second monitor peptide and said labeled version of said second monitor peptide using a mass spectrometer, dividing said measured amount of said second monitor peptide by said measured amount of said labeled version of said second monitor peptide to produce a second ratio, and multiplying said second ratio by the known amount of said labeled version of said second peptide to yield an amount of said second peptide in the digest,
   vii) calculating the relative amounts of said first and second compartments in said sample using the relative amounts of said first and second peptides in the digest, together with previous measurements of the concentrations of said first peptide, or said first protein, in said first compartment and of said second peptide, or said second protein, in said second compartment.

2. A method for measuring the relative amounts of a first and a second compartment of a biological sample comprising:
   i) selecting a first monitor peptide that is proteotypic for a first protein whose amount in said sample is contributed predominantly by said first compartment,
   ii) selecting a second monitor peptide that is proteotypic for a second protein whose amount in said sample is contributed predominantly by said second compartment,
   iii) digesting said sample by means of a proteolytic process to produce a digest,
   iv) adding to said digest labeled versions of said first and second peptides, differing respectively from said first and second peptides by a mass increment, in relative amounts,
   v) measuring the amounts of said first monitor peptide and said labeled version of said first monitor peptide using a mass spectrometer, dividing said measured amount of said first monitor peptide by said measured amount of said labeled version of said first monitor peptide, to yield a relative amount of said first peptide in the digest, vi) measuring the amounts of said second monitor peptide and said labeled version of said second monitor peptide using a mass spectrometer, dividing said measured amount of said second monitor peptide by said measured amount of said labeled version of said second monitor peptide, to yield a relative amount of said second peptide in the digest, vii) calculating the relative amounts of said first and second compartments in said sample using the relative amounts of said first and second peptides in the digest, together with the relative amounts of said labeled versions of said first and second monitor peptides and previous measurements of the concentrations of said first peptide, or said first protein, in said first compartment and of said second peptide, or said second protein, in said second compartment.

3. The method of claim 1, wherein said sample is a blood sample, said first compartment is plasma and said second compartment is red blood cells.

4. The method of claim 1, wherein one of said compartments is a plasma compartment and at least one of said monitor peptides comprises a peptide selected from Seq ID 1-5 (HSA); Seq ID 6-10 (immunoglobulins); Seq ID 11-15 (transferrin); and Seq ID 16-20 (alpha-2-macroglobulin).

5. The method of claim 1, wherein one of said compartments is a red blood cell compartment and at least one of said monitor peptides comprises a peptide selected from Seq ID 21-24 (Hb alpha), Seq ID 25-29 (Hb beta) and Seq ID 30-34 (carbonic anhydrase 1).

6. The method of claim 4, wherein said relative amounts are used to calculate a hematocrit value of said blood sample.

7. The method of claim 5, wherein said relative amounts are used to calculate a hematocrit value of said blood sample.

8. The method of claim 6, wherein said sample is a dried blood sample.

9. The method of claim 7, wherein said sample is a dried blood sample.

10. The method of claim 3, wherein said amounts of said first and second compartments are combined to estimate the total amount of blood in said sample.

11. The method of claim 1, wherein the amounts of said first and second compartments are combined to estimate the total amount of sample.

12. The method of claim 1, wherein said amount of said first compartment comprises the sum of the amounts of a red blood cell compartment and a plasma compartment, and said second compartment is selected from the group consisting of platelets, lymphocytes, monocytes, neutrophil granulocytes, eosinophils and basophils.

* * * * *

SEQUENCE LISTING

<160> NUMBER OF SEQ ID NOS: 137

<210> SEQ ID NO 1
<211> LENGTH: 10
<212> TYPE: PRT
<213> ORGANISM: Artificial Sequence
<220> FEATURE:
<223> OTHER INFORMATION: peptide

<400> SEQUENCE: 1

Leu Val Asn Glu Val Thr Glu Phe Ala Lys
1               5                   10

<210> SEQ ID NO 2
<211> LENGTH: 21
<212> TYPE: PRT
<213> ORGANISM: Artificial Sequence
<220> FEATURE:
<223> OTHER INFORMATION: peptide

<400> SEQUENCE: 2

Ala Leu Val Leu Ile Ala Phe Ala Gln Tyr Leu Gln Gln Cys Pro Phe
1               5                   10                  15

Glu Asp His Val Lys
            20

<210> SEQ ID NO 3
<211> LENGTH: 7
<212> TYPE: PRT
<213> ORGANISM: Artificial Sequence
<220> FEATURE:

```
<223> OTHER INFORMATION: peptide

<400> SEQUENCE: 3

Tyr Leu Tyr Glu Ile Ala Arg
1               5

<210> SEQ ID NO 4
<211> LENGTH: 13
<212> TYPE: PRT
<213> ORGANISM: Artificial Sequence
<220> FEATURE:
<223> OTHER INFORMATION: peptide

<400> SEQUENCE: 4

Asp Val Phe Leu Gly Met Phe Leu Tyr Glu Tyr Ala Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: peptide

<400> SEQUENCE: 5

Phe Ser Ala Leu Glu Val Asp Glu Thr Tyr Val Pro Lys
1               5                   10

<210> SEQ ID NO 6
<211> LENGTH: 15
<212> TYPE: PRT
<213> ORGANISM: Artificial Sequence
<220> FEATURE:
<223> OTHER INFORMATION: peptide

<400> SEQUENCE: 6

Tyr Ala Ala Ser Ser Tyr Leu Ser Leu Thr Pro Glu Gln Trp Lys
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: peptide

<400> SEQUENCE: 7

Ala Gly Val Glu Thr Thr Thr Pro Ser Lys
1               5                   10

<210> SEQ ID NO 8
<211> LENGTH: 19
<212> TYPE: PRT
<213> ORGANISM: Artificial Sequence
<220> FEATURE:
<223> OTHER INFORMATION: peptide

<400> SEQUENCE: 8

Ala Ala Pro Ser Val Thr Leu Phe Pro Pro Ser Ser Glu Glu Leu Gln
1               5                   10                  15

Ala Asn Lys

<210> SEQ ID NO 9
<211> LENGTH: 14
<212> TYPE: PRT
<213> ORGANISM: Artificial Sequence
```

<220> FEATURE:
<223> OTHER INFORMATION: peptide

<400> SEQUENCE: 9

Asp Ser Thr Tyr Ser Leu Ser Ser Thr Leu Thr Leu Ser Lys
1               5                   10

<210> SEQ ID NO 10
<211> LENGTH: 18
<212> TYPE: PRT
<213> ORGANISM: Artificial Sequence
<220> FEATURE:
<223> OTHER INFORMATION: peptide

<400> SEQUENCE: 10

Thr Val Ala Ala Pro Ser Val Phe Ile Phe Pro Pro Ser Asp Glu Gln
1               5                   10                  15

Leu Lys

<210> SEQ ID NO 11
<211> LENGTH: 14
<212> TYPE: PRT
<213> ORGANISM: Artificial Sequence
<220> FEATURE:
<223> OTHER INFORMATION: peptide

<400> SEQUENCE: 11

Glu Asp Pro Gln Thr Phe Tyr Tyr Ala Val Ala Val Val Lys
1               5                   10

<210> SEQ ID NO 12
<211> LENGTH: 21
<212> TYPE: PRT
<213> ORGANISM: Artificial Sequence
<220> FEATURE:
<223> OTHER INFORMATION: peptide

<400> SEQUENCE: 12

Gln Gln Gln His Leu Phe Gly Ser Asn Val Thr Asp Cys Ser Gly Asn
1               5                   10                  15

Phe Cys Leu Phe Arg
            20

<210> SEQ ID NO 13
<211> LENGTH: 12
<212> TYPE: PRT
<213> ORGANISM: Artificial Sequence
<220> FEATURE:
<223> OTHER INFORMATION: peptide

<400> SEQUENCE: 13

Met Tyr Leu Gly Tyr Glu Tyr Val Thr Ala Ile Arg
1               5                   10

<210> SEQ ID NO 14
<211> LENGTH: 15
<212> TYPE: PRT
<213> ORGANISM: Artificial Sequence
<220> FEATURE:
<223> OTHER INFORMATION: peptide

<400> SEQUENCE: 14

Ile Glu Cys Val Ser Ala Glu Thr Thr Glu Asp Cys Ile Ala Lys
1               5                   10                  15

```
<210> SEQ ID NO 15
<211> LENGTH: 15
<212> TYPE: PRT
<213> ORGANISM: Artificial Sequence
<220> FEATURE:
<223> OTHER INFORMATION: peptide

<400> SEQUENCE: 15

Leu Cys Met Gly Ser Gly Leu Asn Leu Cys Glu Pro Asn Asn Lys
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: peptide

<400> SEQUENCE: 16

Asn Glu Asp Ser Leu Val Phe Val Gln Thr Asp Lys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: peptide

<400> SEQUENCE: 17

Ser Ser Gly Ser Leu Leu Asn Asn Ala Ile Lys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: peptide

<400> SEQUENCE: 18

Asn Gln Gly Asn Thr Trp Leu Thr Ala Phe Val Leu Lys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: peptide

<400> SEQUENCE: 19

Val Gly Phe Tyr Glu Ser Asp Val Met Gly Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: peptide

<400> SEQUENCE: 20

Ala Ile Gly Tyr Leu Asn Thr Gly Tyr Gln Arg
1               5                   10

<210> SEQ ID NO 21
```

```
<211> LENGTH: 11
<212> TYPE: PRT
<213> ORGANISM: Artificial Sequence
<220> FEATURE:
<223> OTHER INFORMATION: peptide

<400> SEQUENCE: 21

Ala Gly Glu Tyr Gly Ala Glu Ala Leu Glu Arg
1               5                   10

<210> SEQ ID NO 22
<211> LENGTH: 11
<212> TYPE: PRT
<213> ORGANISM: Artificial Sequence
<220> FEATURE:
<223> OTHER INFORMATION: peptide

<400> SEQUENCE: 22

Leu Ala Ser Val Ser Thr Val Leu Thr Ser Lys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: peptide

<400> SEQUENCE: 23

Ala Ser Val Ser Thr Val Leu Thr Ser Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: peptide

<400> SEQUENCE: 24

Gly Glu Tyr Gly Ala Glu Ala Leu Glu Arg
1               5                   10

<210> SEQ ID NO 25
<211> LENGTH: 8
<212> TYPE: PRT
<213> ORGANISM: Artificial Sequence
<220> FEATURE:
<223> OTHER INFORMATION: peptide

<400> SEQUENCE: 25

Val His Leu Thr Pro Glu Glu Lys
1               5

<210> SEQ ID NO 26
<211> LENGTH: 9
<212> TYPE: PRT
<213> ORGANISM: Artificial Sequence
<220> FEATURE:
<223> OTHER INFORMATION: peptide

<400> SEQUENCE: 26

Leu Val Val Tyr Pro Trp Thr Gln Arg
1               5

<210> SEQ ID NO 27
<211> LENGTH: 11
```

```
<212> TYPE: PRT
<213> ORGANISM: Artificial Sequence
<220> FEATURE:
<223> OTHER INFORMATION: peptide

<400> SEQUENCE: 27

Val Asp Glu Val Gly Gly Glu Ala Leu Gly Arg
1               5                   10

<210> SEQ ID NO 28
<211> LENGTH: 14
<212> TYPE: PRT
<213> ORGANISM: Artificial Sequence
<220> FEATURE:
<223> OTHER INFORMATION: peptide

<400> SEQUENCE: 28

Gly Asp Leu Ser Thr Pro Asp Ala Val Met Gly Asn Pro Lys
1               5                   10

<210> SEQ ID NO 29
<211> LENGTH: 11
<212> TYPE: PRT
<213> ORGANISM: Artificial Sequence
<220> FEATURE:
<223> OTHER INFORMATION: peptide

<400> SEQUENCE: 29

Ser Thr Pro Asp Ala Val Met Gly Asn Pro Lys
1               5                   10

<210> SEQ ID NO 30
<211> LENGTH: 9
<212> TYPE: PRT
<213> ORGANISM: Artificial Sequence
<220> FEATURE:
<223> OTHER INFORMATION: peptide

<400> SEQUENCE: 30

Gly Gly Pro Phe Ser Asp Ser Tyr Arg
1               5

<210> SEQ ID NO 31
<211> LENGTH: 10
<212> TYPE: PRT
<213> ORGANISM: Artificial Sequence
<220> FEATURE:
<223> OTHER INFORMATION: peptide

<400> SEQUENCE: 31

Gly Leu Ala Val Ile Gly Val Leu Met Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: peptide

<400> SEQUENCE: 32

Ala Ser Pro Asp Trp Gly Tyr Asp Asp Lys
1               5                   10

<210> SEQ ID NO 33
<211> LENGTH: 11
<212> TYPE: PRT
```

```
<213> ORGANISM: Artificial Sequence
<220> FEATURE:
<223> OTHER INFORMATION: peptide

<400> SEQUENCE: 33

Asp Gly Leu Ala Val Ile Gly Val Leu Met Lys
1               5                   10

<210> SEQ ID NO 34
<211> LENGTH: 13
<212> TYPE: PRT
<213> ORGANISM: Artificial Sequence
<220> FEATURE:
<223> OTHER INFORMATION: peptide

<400> SEQUENCE: 34

Ser Ile Ser Val Ser Ser Glu Gln Leu Ala Gln Phe Arg
1               5                   10

<210> SEQ ID NO 35
<211> LENGTH: 12
<212> TYPE: PRT
<213> ORGANISM: Artificial Sequence
<220> FEATURE:
<223> OTHER INFORMATION: peptide

<400> SEQUENCE: 35

Thr Leu Ile Leu Asp Val Pro Pro Gly Val Glu Lys
1               5                   10

<210> SEQ ID NO 36
<211> LENGTH: 11
<212> TYPE: PRT
<213> ORGANISM: Artificial Sequence
<220> FEATURE:
<223> OTHER INFORMATION: peptide

<400> SEQUENCE: 36

Phe Gln Cys Gly Asn Met Ile Phe Asp Asn Lys
1               5                   10

<210> SEQ ID NO 37
<211> LENGTH: 11
<212> TYPE: PRT
<213> ORGANISM: Artificial Sequence
<220> FEATURE:
<223> OTHER INFORMATION: peptide

<400> SEQUENCE: 37

Leu Phe Leu Ala Glu Phe Gln Ser Ile Pro Arg
1               5                   10

<210> SEQ ID NO 38
<211> LENGTH: 9
<212> TYPE: PRT
<213> ORGANISM: Artificial Sequence
<220> FEATURE:
<223> OTHER INFORMATION: peptide

<400> SEQUENCE: 38

Asp Glu Thr Val Asp Asp Phe Trp Arg
1               5

<210> SEQ ID NO 39
<211> LENGTH: 11
<212> TYPE: PRT
<213> ORGANISM: Artificial Sequence
```

```
<220> FEATURE:
<223> OTHER INFORMATION: peptide

<400> SEQUENCE: 39

Asp Leu Gln Tyr Ser Thr Asp Tyr Thr Phe Lys
1               5                   10

<210> SEQ ID NO 40
<211> LENGTH: 9
<212> TYPE: PRT
<213> ORGANISM: Artificial Sequence
<220> FEATURE:
<223> OTHER INFORMATION: peptide

<400> SEQUENCE: 40

Tyr Ala Phe Val Asn Trp Ile Asn Lys
1               5

<210> SEQ ID NO 41
<211> LENGTH: 14
<212> TYPE: PRT
<213> ORGANISM: Artificial Sequence
<220> FEATURE:
<223> OTHER INFORMATION: peptide

<400> SEQUENCE: 41

Val Tyr Ala Leu Pro Glu Asp Leu Val Glu Val Asn Pro Lys
1               5                   10

<210> SEQ ID NO 42
<211> LENGTH: 9
<212> TYPE: PRT
<213> ORGANISM: Artificial Sequence
<220> FEATURE:
<223> OTHER INFORMATION: peptide

<400> SEQUENCE: 42

Leu Ser Pro Glu Glu Leu Leu Leu Arg
1               5

<210> SEQ ID NO 43
<211> LENGTH: 16
<212> TYPE: PRT
<213> ORGANISM: Artificial Sequence
<220> FEATURE:
<223> OTHER INFORMATION: peptide

<400> SEQUENCE: 43

Phe Ser Leu Val Gly Ile Gly Gly Gln Asp Leu Asn Glu Gly Asn Arg
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: peptide

<400> SEQUENCE: 44

Gly Ser Val Ser Asp Glu Glu Met Met Glu Leu Arg
1               5                   10

<210> SEQ ID NO 45
<211> LENGTH: 14
<212> TYPE: PRT
<213> ORGANISM: Artificial Sequence
<220> FEATURE:
```

```
<223> OTHER INFORMATION: peptide

<400> SEQUENCE: 45

Asn Pro Asp Gly Pro Asp Pro Ala Trp Gly Gly Gly Gly Arg
1               5                   10

<210> SEQ ID NO 46
<211> LENGTH: 14
<212> TYPE: PRT
<213> ORGANISM: Artificial Sequence
<220> FEATURE:
<223> OTHER INFORMATION: peptide

<400> SEQUENCE: 46

Gly Thr Ser Asp Gly Pro Thr Gln Gln Leu Thr Trp Ser Arg
1               5                   10

<210> SEQ ID NO 47
<211> LENGTH: 15
<212> TYPE: PRT
<213> ORGANISM: Artificial Sequence
<220> FEATURE:
<223> OTHER INFORMATION: peptide

<400> SEQUENCE: 47

Gly Asn Val Leu Ser Leu Pro Thr Pro Thr Ser Gly Leu Gly Arg
1               5                   10                  15

<210> SEQ ID NO 48
<211> LENGTH: 13
<212> TYPE: PRT
<213> ORGANISM: Artificial Sequence
<220> FEATURE:
<223> OTHER INFORMATION: peptide

<400> SEQUENCE: 48

Asp Met Trp Val Met Glu Thr Gly Leu Leu Leu Pro Arg
1               5                   10

<210> SEQ ID NO 49
<211> LENGTH: 15
<212> TYPE: PRT
<213> ORGANISM: Artificial Sequence
<220> FEATURE:
<223> OTHER INFORMATION: peptide

<400> SEQUENCE: 49

Asn Pro Ser Ser Asp Val Gln Ala Asp Gly Ala Leu Gly Ser Arg
1               5                   10                  15

<210> SEQ ID NO 50
<211> LENGTH: 13
<212> TYPE: PRT
<213> ORGANISM: Artificial Sequence
<220> FEATURE:
<223> OTHER INFORMATION: peptide

<400> SEQUENCE: 50

Asn Ser Val Asn Gly Thr Phe Pro Ala Glu Pro Met Lys
1               5                   10

<210> SEQ ID NO 51
<211> LENGTH: 19
<212> TYPE: PRT
<213> ORGANISM: Artificial Sequence
<220> FEATURE:
<223> OTHER INFORMATION: peptide
```

-continued

<400> SEQUENCE: 51

Ala His Thr Pro Tyr Ile Asn Ile Tyr Asn Cys Glu Pro Ala Asn Pro
1               5                   10                  15

Ser Glu Lys

<210> SEQ ID NO 52
<211> LENGTH: 11
<212> TYPE: PRT
<213> ORGANISM: Artificial Sequence
<220> FEATURE:
<223> OTHER INFORMATION: peptide

<400> SEQUENCE: 52

Ser Asn Ile Val Leu Leu Ser Ala Glu Glu Lys
1               5                   10

<210> SEQ ID NO 53
<211> LENGTH: 13
<212> TYPE: PRT
<213> ORGANISM: Artificial Sequence
<220> FEATURE:
<223> OTHER INFORMATION: peptide

<400> SEQUENCE: 53

Ile Lys Asp Leu Ala His Gln Phe Thr Gln Val Gln Arg
1               5                   10

<210> SEQ ID NO 54
<211> LENGTH: 13
<212> TYPE: PRT
<213> ORGANISM: Artificial Sequence
<220> FEATURE:
<223> OTHER INFORMATION: peptide

<400> SEQUENCE: 54

Val Gln Thr Leu Glu Ala Trp Val Ile His Gly Gly Arg
1               5                   10

<210> SEQ ID NO 55
<211> LENGTH: 11
<212> TYPE: PRT
<213> ORGANISM: Artificial Sequence
<220> FEATURE:
<223> OTHER INFORMATION: peptide

<400> SEQUENCE: 55

Asp Leu Ala His Gln Phe Thr Gln Val Gln Arg
1               5                   10

<210> SEQ ID NO 56
<211> LENGTH: 9
<212> TYPE: PRT
<213> ORGANISM: Artificial Sequence
<220> FEATURE:
<223> OTHER INFORMATION: peptide

<400> SEQUENCE: 56

Asp Leu Cys Gln Asp Pro Thr Ile Lys
1               5

<210> SEQ ID NO 57
<211> LENGTH: 10
<212> TYPE: PRT
<213> ORGANISM: Artificial Sequence
<220> FEATURE:

<223> OTHER INFORMATION: peptide

<400> SEQUENCE: 57

Ile Asn Tyr Gln Ser Cys Pro Asp Trp Arg
1               5                   10

<210> SEQ ID NO 58
<211> LENGTH: 13
<212> TYPE: PRT
<213> ORGANISM: Artificial Sequence
<220> FEATURE:
<223> OTHER INFORMATION: peptide

<400> SEQUENCE: 58

Val Ser Met Ser Pro Gly Asp Gln Val Met Glu Gly Lys
1               5                   10

<210> SEQ ID NO 59
<211> LENGTH: 18
<212> TYPE: PRT
<213> ORGANISM: Artificial Sequence
<220> FEATURE:
<223> OTHER INFORMATION: peptide

<400> SEQUENCE: 59

Tyr Glu Trp Lys Pro His Gly Ala Trp Glu Glu Pro Ser Leu Gly Val
1               5                   10                  15

Leu Lys

<210> SEQ ID NO 60
<211> LENGTH: 13
<212> TYPE: PRT
<213> ORGANISM: Artificial Sequence
<220> FEATURE:
<223> OTHER INFORMATION: peptide

<400> SEQUENCE: 60

Tyr Cys Cys Gln Val Ser Asn Asp Val Gly Pro Gly Arg
1               5                   10

<210> SEQ ID NO 61
<211> LENGTH: 20
<212> TYPE: PRT
<213> ORGANISM: Artificial Sequence
<220> FEATURE:
<223> OTHER INFORMATION: peptide

<400> SEQUENCE: 61

Glu Gly Asp Thr Val Thr Leu Ser Cys Asn Tyr Asn Ser Ser Asn Pro
1               5                   10                  15

Ser Val Thr Arg
            20

<210> SEQ ID NO 62
<211> LENGTH: 17
<212> TYPE: PRT
<213> ORGANISM: Artificial Sequence
<220> FEATURE:
<223> OTHER INFORMATION: peptide

<400> SEQUENCE: 62

Ser Pro Leu Ser Thr Leu Thr Val Tyr Tyr Ser Pro Glu Thr Ile Gly
1               5                   10                  15

Arg

<210> SEQ ID NO 63
<211> LENGTH: 9
<212> TYPE: PRT
<213> ORGANISM: Artificial Sequence
<220> FEATURE:
<223> OTHER INFORMATION: peptide

<400> SEQUENCE: 63

Asp Leu Tyr Ser Gly Leu Asn Gln Arg
1               5

<210> SEQ ID NO 64
<211> LENGTH: 14
<212> TYPE: PRT
<213> ORGANISM: Artificial Sequence
<220> FEATURE:
<223> OTHER INFORMATION: peptide

<400> SEQUENCE: 64

Gly Ser Lys Pro Glu Asp Ala Asn Phe Tyr Leu Tyr Leu Arg
1               5                   10

<210> SEQ ID NO 65
<211> LENGTH: 16
<212> TYPE: PRT
<213> ORGANISM: Artificial Sequence
<220> FEATURE:
<223> OTHER INFORMATION: peptide

<400> SEQUENCE: 65

Gln Asp Gly Asn Glu Glu Met Gly Gly Ile Thr Gln Thr Pro Tyr Lys
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: peptide

<400> SEQUENCE: 66

Glu Phe Ser Glu Leu Glu Gln Ser Gly Tyr Tyr Val Cys Tyr Pro Arg
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: peptide

<400> SEQUENCE: 67

Glu Arg Pro Pro Pro Val Pro Asn Pro Asp Tyr Glu Pro Ile Arg
1               5                   10                  15

<210> SEQ ID NO 68
<211> LENGTH: 12
<212> TYPE: PRT
<213> ORGANISM: Artificial Sequence
<220> FEATURE:
<223> OTHER INFORMATION: peptide

<400> SEQUENCE: 68

Phe Ile Val Leu Ser Asn Asn Tyr Leu Gln Ile Arg
1               5                   10

```
<210> SEQ ID NO 69
<211> LENGTH: 13
<212> TYPE: PRT
<213> ORGANISM: Artificial Sequence
<220> FEATURE:
<223> OTHER INFORMATION: peptide

<400> SEQUENCE: 69

Leu Glu Gly Gln Met Gly Glu Asp Gly Asn Ser Ile Lys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: peptide

<400> SEQUENCE: 70

Gly Leu Gly Glu Ile Ser Ala Ala Ser Glu Phe Lys
1               5                   10

<210> SEQ ID NO 71
<211> LENGTH: 11
<212> TYPE: PRT
<213> ORGANISM: Artificial Sequence
<220> FEATURE:
<223> OTHER INFORMATION: peptide

<400> SEQUENCE: 71

Leu Pro Ser Gly Ser Asp His Val Met Leu Lys
1               5                   10

<210> SEQ ID NO 72
<211> LENGTH: 11
<212> TYPE: PRT
<213> ORGANISM: Artificial Sequence
<220> FEATURE:
<223> OTHER INFORMATION: peptide

<400> SEQUENCE: 72

Ala Gly Glu Gln Asp Ala Thr Ile His Leu Lys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: peptide

<400> SEQUENCE: 73

Ser Leu Trp Asp Gln Gly Asn Phe Pro Leu Ile Ile Lys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: peptide

<400> SEQUENCE: 74

Leu Thr Gly Ser Gly Glu Leu Trp Trp Gln Ala Glu Arg
1               5                   10

<210> SEQ ID NO 75
```

```
<211> LENGTH: 10
<212> TYPE: PRT
<213> ORGANISM: Artificial Sequence
<220> FEATURE:
<223> OTHER INFORMATION: peptide

<400> SEQUENCE: 75

Ile Asp Ile Val Val Leu Ala Phe Gln Lys
1               5                   10

<210> SEQ ID NO 76
<211> LENGTH: 11
<212> TYPE: PRT
<213> ORGANISM: Artificial Sequence
<220> FEATURE:
<223> OTHER INFORMATION: peptide

<400> SEQUENCE: 76

Ile Leu Gly Asn Gln Gly Ser Phe Leu Thr Lys
1               5                   10

<210> SEQ ID NO 77
<211> LENGTH: 17
<212> TYPE: PRT
<213> ORGANISM: Artificial Sequence
<220> FEATURE:
<223> OTHER INFORMATION: peptide

<400> SEQUENCE: 77

Glu Gly Glu Gln Val Glu Phe Ser Phe Pro Leu Ala Phe Thr Val Glu
1               5                   10                  15

Lys

<210> SEQ ID NO 78
<211> LENGTH: 11
<212> TYPE: PRT
<213> ORGANISM: Artificial Sequence
<220> FEATURE:
<223> OTHER INFORMATION: peptide

<400> SEQUENCE: 78

Val Phe Thr Glu Gly Glu Pro Leu Ala Leu Arg
1               5                   10

<210> SEQ ID NO 79
<211> LENGTH: 9
<212> TYPE: PRT
<213> ORGANISM: Artificial Sequence
<220> FEATURE:
<223> OTHER INFORMATION: peptide

<400> SEQUENCE: 79

Val Ile Ser Ser Leu Gln Glu Asp Arg
1               5

<210> SEQ ID NO 80
<211> LENGTH: 9
<212> TYPE: PRT
<213> ORGANISM: Artificial Sequence
<220> FEATURE:
<223> OTHER INFORMATION: peptide

<400> SEQUENCE: 80

Leu Val Tyr Asn Val Leu Tyr Tyr Arg
1               5
```

```
<210> SEQ ID NO 81
<211> LENGTH: 14
<212> TYPE: PRT
<213> ORGANISM: Artificial Sequence
<220> FEATURE:
<223> OTHER INFORMATION: peptide

<400> SEQUENCE: 81

Thr Thr Pro Glu Pro Cys Glu Leu Asp Asp Glu Asp Phe Arg
1               5                   10

<210> SEQ ID NO 82
<211> LENGTH: 9
<212> TYPE: PRT
<213> ORGANISM: Artificial Sequence
<220> FEATURE:
<223> OTHER INFORMATION: peptide

<400> SEQUENCE: 82

Ala Thr Val Asn Pro Ser Ala Pro Arg
1               5

<210> SEQ ID NO 83
<211> LENGTH: 14
<212> TYPE: PRT
<213> ORGANISM: Artificial Sequence
<220> FEATURE:
<223> OTHER INFORMATION: peptide

<400> SEQUENCE: 83

Thr Ser Leu Asp Leu Ser Asp Asn Pro Gly Leu Gly Glu Arg
1               5                   10

<210> SEQ ID NO 84
<211> LENGTH: 11
<212> TYPE: PRT
<213> ORGANISM: Artificial Sequence
<220> FEATURE:
<223> OTHER INFORMATION: peptide

<400> SEQUENCE: 84

Ser Trp Leu Ala Glu Leu Gln Gln Trp Leu Lys
1               5                   10

<210> SEQ ID NO 85
<211> LENGTH: 13
<212> TYPE: PRT
<213> ORGANISM: Artificial Sequence
<220> FEATURE:
<223> OTHER INFORMATION: peptide

<400> SEQUENCE: 85

Thr Pro Glu Pro Cys Glu Leu Asp Asp Glu Asp Phe Arg
1               5                   10

<210> SEQ ID NO 86
<211> LENGTH: 14
<212> TYPE: PRT
<213> ORGANISM: Artificial Sequence
<220> FEATURE:
<223> OTHER INFORMATION: peptide

<400> SEQUENCE: 86

Ala Gly Tyr Leu Gly Tyr Thr Val Thr Trp Leu Pro Ser Arg
1               5                   10

<210> SEQ ID NO 87
```

<211> LENGTH: 10
<212> TYPE: PRT
<213> ORGANISM: Artificial Sequence
<220> FEATURE:
<223> OTHER INFORMATION: peptide

<400> SEQUENCE: 87

Thr Ser Leu Leu Ala Ser Gly Ala Pro Arg
1               5                   10

<210> SEQ ID NO 88
<211> LENGTH: 22
<212> TYPE: PRT
<213> ORGANISM: Artificial Sequence
<220> FEATURE:
<223> OTHER INFORMATION: peptide

<400> SEQUENCE: 88

Gly Asn Val Asp Leu Val Phe Leu Phe Asp Gly Ser Met Ser Leu Gln
1               5                   10                  15

Pro Asp Glu Phe Gln Lys
            20

<210> SEQ ID NO 89
<211> LENGTH: 10
<212> TYPE: PRT
<213> ORGANISM: Artificial Sequence
<220> FEATURE:
<223> OTHER INFORMATION: peptide

<400> SEQUENCE: 89

Asp Trp Ala Gly Gly Phe Leu Asp Leu Lys
1               5                   10

<210> SEQ ID NO 90
<211> LENGTH: 11
<212> TYPE: PRT
<213> ORGANISM: Artificial Sequence
<220> FEATURE:
<223> OTHER INFORMATION: peptide

<400> SEQUENCE: 90

Ile Gly Asn Glu Pro Leu Thr Pro Glu Val Arg
1               5                   10

<210> SEQ ID NO 91
<211> LENGTH: 13
<212> TYPE: PRT
<213> ORGANISM: Artificial Sequence
<220> FEATURE:
<223> OTHER INFORMATION: peptide

<400> SEQUENCE: 91

Asp Tyr Leu Pro Leu Val Leu Gly Pro Thr Ala Met Arg
1               5                   10

<210> SEQ ID NO 92
<211> LENGTH: 10
<212> TYPE: PRT
<213> ORGANISM: Artificial Sequence
<220> FEATURE:
<223> OTHER INFORMATION: peptide

<400> SEQUENCE: 92

Ile Ala Asn Val Phe Thr Asn Ala Phe Arg
1               5                   10

```
<210> SEQ ID NO 93
<211> LENGTH: 12
<212> TYPE: PRT
<213> ORGANISM: Artificial Sequence
<220> FEATURE:
<223> OTHER INFORMATION: peptide

<400> SEQUENCE: 93

Val Val Leu Glu Gly Gly Ile Asp Pro Ile Leu Arg
1               5                   10

<210> SEQ ID NO 94
<211> LENGTH: 12
<212> TYPE: PRT
<213> ORGANISM: Artificial Sequence
<220> FEATURE:
<223> OTHER INFORMATION: peptide

<400> SEQUENCE: 94

Ile Gly Leu Asp Leu Pro Ala Leu Asn Met Gln Arg
1               5                   10

<210> SEQ ID NO 95
<211> LENGTH: 18
<212> TYPE: PRT
<213> ORGANISM: Artificial Sequence
<220> FEATURE:
<223> OTHER INFORMATION: peptide

<400> SEQUENCE: 95

Phe Cys Gly Leu Pro Gln Pro Glu Thr Val Gly Gln Leu Gly Thr Val
1               5                   10                  15

Leu Arg

<210> SEQ ID NO 96
<211> LENGTH: 9
<212> TYPE: PRT
<213> ORGANISM: Artificial Sequence
<220> FEATURE:
<223> OTHER INFORMATION: peptide

<400> SEQUENCE: 96

Asn Trp Ile Asp Ser Ile Ile Gln Arg
1               5

<210> SEQ ID NO 97
<211> LENGTH: 13
<212> TYPE: PRT
<213> ORGANISM: Artificial Sequence
<220> FEATURE:
<223> OTHER INFORMATION: peptide

<400> SEQUENCE: 97

Ala Gln Phe Val Asn Trp Ile Asp Ser Ile Ile Gln Arg
1               5                   10

<210> SEQ ID NO 98
<211> LENGTH: 10
<212> TYPE: PRT
<213> ORGANISM: Artificial Sequence
<220> FEATURE:
<223> OTHER INFORMATION: peptide

<400> SEQUENCE: 98

Leu Ala Met Gly Trp Gly Leu Leu Gly Arg
1               5                   10
```

```
<210> SEQ ID NO 99
<211> LENGTH: 14
<212> TYPE: PRT
<213> ORGANISM: Artificial Sequence
<220> FEATURE:
<223> OTHER INFORMATION: peptide

<400> SEQUENCE: 99

Asn Ala Asn Val Gln Val Ala Gln Leu Pro Ala Gln Gly Arg
1               5                   10

<210> SEQ ID NO 100
<211> LENGTH: 9
<212> TYPE: PRT
<213> ORGANISM: Artificial Sequence
<220> FEATURE:
<223> OTHER INFORMATION: peptide

<400> SEQUENCE: 100

Tyr Gly Thr Cys Ile Tyr Gln Gly Arg
1               5

<210> SEQ ID NO 101
<211> LENGTH: 9
<212> TYPE: PRT
<213> ORGANISM: Artificial Sequence
<220> FEATURE:
<223> OTHER INFORMATION: peptide

<400> SEQUENCE: 101

Ile Pro Ala Cys Ile Ala Gly Glu Arg
1               5

<210> SEQ ID NO 102
<211> LENGTH: 18
<212> TYPE: PRT
<213> ORGANISM: Artificial Sequence
<220> FEATURE:
<223> OTHER INFORMATION: peptide

<400> SEQUENCE: 102

Asp Ile Pro Glu Val Val Val Ser Leu Ala Trp Asp Glu Ser Leu Ala
1               5                   10                  15

Pro Lys

<210> SEQ ID NO 103
<211> LENGTH: 13
<212> TYPE: PRT
<213> ORGANISM: Artificial Sequence
<220> FEATURE:
<223> OTHER INFORMATION: peptide

<400> SEQUENCE: 103

Asn Tyr Thr Pro Gln Leu Ser Glu Ala Glu Val Glu Arg
1               5                   10

<210> SEQ ID NO 104
<211> LENGTH: 15
<212> TYPE: PRT
<213> ORGANISM: Artificial Sequence
<220> FEATURE:
<223> OTHER INFORMATION: peptide

<400> SEQUENCE: 104

Ile Ser Gln Gly Glu Ala Asp Ile Asn Ile Ala Phe Tyr Gln Arg
```

```
1               5                  10                 15
```

<210> SEQ ID NO 105
<211> LENGTH: 10
<212> TYPE: PRT
<213> ORGANISM: Artificial Sequence
<220> FEATURE:
<223> OTHER INFORMATION: peptide

<400> SEQUENCE: 105

```
Tyr Tyr Ala Phe Asp Leu Ile Ala Gln Arg
1               5                  10
```

<210> SEQ ID NO 106
<211> LENGTH: 10
<212> TYPE: PRT
<213> ORGANISM: Artificial Sequence
<220> FEATURE:
<223> OTHER INFORMATION: peptide

<400> SEQUENCE: 106

```
Leu Thr Phe Asp Ala Ile Thr Thr Ile Arg
1               5                  10
```

<210> SEQ ID NO 107
<211> LENGTH: 16
<212> TYPE: PRT
<213> ORGANISM: Artificial Sequence
<220> FEATURE:
<223> OTHER INFORMATION: peptide

<400> SEQUENCE: 107

```
Asp Ala Phe Glu Leu Trp Ser Val Ala Ser Pro Leu Ile Phe Thr Arg
1               5                  10                 15
```

<210> SEQ ID NO 108
<211> LENGTH: 18
<212> TYPE: PRT
<213> ORGANISM: Artificial Sequence
<220> FEATURE:
<223> OTHER INFORMATION: peptide

<400> SEQUENCE: 108

```
Ile Gln Cys Ser Val Ser Ala Leu Asn Gln Gly Gln Val Trp Ile Gly
1               5                  10                 15

Gly Arg
```

<210> SEQ ID NO 109
<211> LENGTH: 13
<212> TYPE: PRT
<213> ORGANISM: Artificial Sequence
<220> FEATURE:
<223> OTHER INFORMATION: peptide

<400> SEQUENCE: 109

```
Ser Leu Gln Thr Phe Ser Gln Ala Trp Phe Thr Cys Arg
1               5                  10
```

<210> SEQ ID NO 110
<211> LENGTH: 14
<212> TYPE: PRT
<213> ORGANISM: Artificial Sequence
<220> FEATURE:
<223> OTHER INFORMATION: peptide

<400> SEQUENCE: 110

Gly Asn Leu Val Ser Ile His Asn Phe Asn Ile Asn Tyr Arg
1               5                   10

<210> SEQ ID NO 111
<211> LENGTH: 11
<212> TYPE: PRT
<213> ORGANISM: Artificial Sequence
<220> FEATURE:
<223> OTHER INFORMATION: peptide

<400> SEQUENCE: 111

Val Val Gly Ile Pro Gly Cys Gln Thr Cys Arg
1               5                   10

<210> SEQ ID NO 112
<211> LENGTH: 13
<212> TYPE: PRT
<213> ORGANISM: Artificial Sequence
<220> FEATURE:
<223> OTHER INFORMATION: peptide

<400> SEQUENCE: 112

Ser Ala Leu Asn Gln Gly Gln Val Trp Ile Gly Gly Arg
1               5                   10

<210> SEQ ID NO 113
<211> LENGTH: 18
<212> TYPE: PRT
<213> ORGANISM: Artificial Sequence
<220> FEATURE:
<223> OTHER INFORMATION: peptide

<400> SEQUENCE: 113

Phe Ala Ser Ala Glu Ala Glu Glu Asp Gly Asp Leu Gln Cys Leu Cys
1               5                   10                  15

Val Lys

<210> SEQ ID NO 114
<211> LENGTH: 9
<212> TYPE: PRT
<213> ORGANISM: Artificial Sequence
<220> FEATURE:
<223> OTHER INFORMATION: peptide

<400> SEQUENCE: 114

His Ile Thr Ser Leu Glu Val Ile Lys
1               5

<210> SEQ ID NO 115
<211> LENGTH: 15
<212> TYPE: PRT
<213> ORGANISM: Artificial Sequence
<220> FEATURE:
<223> OTHER INFORMATION: peptide

<400> SEQUENCE: 115

Ala Gly Pro His Cys Pro Thr Ala Gln Leu Ile Ala Thr Leu Lys
1               5                   10                  15

<210> SEQ ID NO 116
<211> LENGTH: 11
<212> TYPE: PRT
<213> ORGANISM: Artificial Sequence
<220> FEATURE:
<223> OTHER INFORMATION: peptide

<400> SEQUENCE: 116

Ile Cys Leu Asp Leu Gln Ala Pro Leu Tyr Lys
1               5                   10

<210> SEQ ID NO 117
<211> LENGTH: 8
<212> TYPE: PRT
<213> ORGANISM: Artificial Sequence
<220> FEATURE:
<223> OTHER INFORMATION: peptide

<400> SEQUENCE: 117

Thr Thr Ser Gln Val Arg Pro Arg
1               5

<210> SEQ ID NO 118
<211> LENGTH: 12
<212> TYPE: PRT
<213> ORGANISM: Artificial Sequence
<220> FEATURE:
<223> OTHER INFORMATION: peptide

<400> SEQUENCE: 118

Ile Gly Asp Thr Val Ser Phe Ser Ile Glu Ala Lys
1               5                   10

<210> SEQ ID NO 119
<211> LENGTH: 15
<212> TYPE: PRT
<213> ORGANISM: Artificial Sequence
<220> FEATURE:
<223> OTHER INFORMATION: peptide

<400> SEQUENCE: 119

Gly Ser Gly Asp Ser Ser Gln Val Thr Gln Val Ser Pro Gln Arg
1               5                   10                  15

<210> SEQ ID NO 120
<211> LENGTH: 11
<212> TYPE: PRT
<213> ORGANISM: Artificial Sequence
<220> FEATURE:
<223> OTHER INFORMATION: peptide

<400> SEQUENCE: 120

Tyr Cys Glu Cys Asp Asp Phe Ser Cys Val Arg
1               5                   10

<210> SEQ ID NO 121
<211> LENGTH: 12
<212> TYPE: PRT
<213> ORGANISM: Artificial Sequence
<220> FEATURE:
<223> OTHER INFORMATION: peptide

<400> SEQUENCE: 121

Asp Asp Leu Trp Ser Ile Gln Asn Leu Gly Thr Lys
1               5                   10

<210> SEQ ID NO 122
<211> LENGTH: 10
<212> TYPE: PRT
<213> ORGANISM: Artificial Sequence
<220> FEATURE:
<223> OTHER INFORMATION: peptide

<400> SEQUENCE: 122

```
Val Leu Thr Leu Thr Asp Gln Val Thr Arg
1               5                   10
```

<210> SEQ ID NO 123
<211> LENGTH: 10
<212> TYPE: PRT
<213> ORGANISM: Artificial Sequence
<220> FEATURE:
<223> OTHER INFORMATION: peptide

<400> SEQUENCE: 123

```
Asn Ile Gln Ser Leu Glu Val Ile Gly Lys
1               5                   10
```

<210> SEQ ID NO 124
<211> LENGTH: 11
<212> TYPE: PRT
<213> ORGANISM: Artificial Sequence
<220> FEATURE:
<223> OTHER INFORMATION: peptide

<400> SEQUENCE: 124

```
Ser Leu Asp Ser Asp Leu Tyr Ala Glu Leu Arg
1               5                   10
```

<210> SEQ ID NO 125
<211> LENGTH: 10
<212> TYPE: PRT
<213> ORGANISM: Artificial Sequence
<220> FEATURE:
<223> OTHER INFORMATION: peptide

<400> SEQUENCE: 125

```
Asn Gln Val Glu Val Ile Ala Thr Leu Lys
1               5                   10
```

<210> SEQ ID NO 126
<211> LENGTH: 14
<212> TYPE: PRT
<213> ORGANISM: Artificial Sequence
<220> FEATURE:
<223> OTHER INFORMATION: peptide

<400> SEQUENCE: 126

```
Gly Thr His Cys Asn Gln Val Glu Val Ile Ala Thr Leu Lys
1               5                   10
```

<210> SEQ ID NO 127
<211> LENGTH: 9
<212> TYPE: PRT
<213> ORGANISM: Artificial Sequence
<220> FEATURE:
<223> OTHER INFORMATION: peptide

<400> SEQUENCE: 127

```
Ile Cys Leu Asp Pro Asp Ala Pro Arg
1               5
```

<210> SEQ ID NO 128
<211> LENGTH: 14
<212> TYPE: PRT
<213> ORGANISM: Artificial Sequence
<220> FEATURE:
<223> OTHER INFORMATION: peptide

<400> SEQUENCE: 128

```
Gly Gln Val Leu Val Phe Leu Gly Gln Ser Glu Gly Leu Arg
```

```
1               5                   10
```

<210> SEQ ID NO 129
<211> LENGTH: 9
<212> TYPE: PRT
<213> ORGANISM: Artificial Sequence
<220> FEATURE:
<223> OTHER INFORMATION: peptide

<400> SEQUENCE: 129

```
Ile Val Leu Leu Asp Val Pro Val Arg
1               5
```

<210> SEQ ID NO 130
<211> LENGTH: 11
<212> TYPE: PRT
<213> ORGANISM: Artificial Sequence
<220> FEATURE:
<223> OTHER INFORMATION: peptide

<400> SEQUENCE: 130

```
Asn Val Gly Ser Gln Thr Leu Gln Thr Phe Lys
1               5                   10
```

<210> SEQ ID NO 131
<211> LENGTH: 11
<212> TYPE: PRT
<213> ORGANISM: Artificial Sequence
<220> FEATURE:
<223> OTHER INFORMATION: peptide

<400> SEQUENCE: 131

```
Gly Glu Ala Gln Val Trp Thr Gln Leu Leu Arg
1               5                   10
```

<210> SEQ ID NO 132
<211> LENGTH: 10
<212> TYPE: PRT
<213> ORGANISM: Artificial Sequence
<220> FEATURE:
<223> OTHER INFORMATION: peptide

<400> SEQUENCE: 132

```
Ala Leu Ser Asn Val Glu Gly Phe Glu Arg
1               5                   10
```

<210> SEQ ID NO 133
<211> LENGTH: 10
<212> TYPE: PRT
<213> ORGANISM: Artificial Sequence
<220> FEATURE:
<223> OTHER INFORMATION: peptide

<400> SEQUENCE: 133

```
Tyr Thr Asp Leu Val Ala Ile Gln Asn Lys
1               5                   10
```

<210> SEQ ID NO 134
<211> LENGTH: 12
<212> TYPE: PRT
<213> ORGANISM: Artificial Sequence
<220> FEATURE:
<223> OTHER INFORMATION: peptide

<400> SEQUENCE: 134

```
Trp Thr Asp Ser Pro Pro Met Cys Glu Ala Ile Lys
1               5                   10
```

```
<210> SEQ ID NO 135
<211> LENGTH: 14
<212> TYPE: PRT
<213> ORGANISM: Artificial Sequence
<220> FEATURE:
<223> OTHER INFORMATION: peptide

<400> SEQUENCE: 135

Leu Glu Gly Pro Asn Asn Val Glu Cys Thr Thr Ser Gly Arg
1               5                   10

<210> SEQ ID NO 136
<211> LENGTH: 11
<212> TYPE: PRT
<213> ORGANISM: Artificial Sequence
<220> FEATURE:
<223> OTHER INFORMATION: peptide

<400> SEQUENCE: 136

Asn Asn Glu Asp Cys Val Glu Ile Tyr Ile Lys
1               5                   10

<210> SEQ ID NO 137
<211> LENGTH: 10
<212> TYPE: PRT
<213> ORGANISM: Artificial Sequence
<220> FEATURE:
<223> OTHER INFORMATION: peptide

<400> SEQUENCE: 137

Tyr Ser Ser Tyr Tyr Trp Ile Gly Ile Arg
1               5                   10
```